United States Patent
Nakamura et al.

(10) Patent No.: US 9,655,698 B2
(45) Date of Patent: May 23, 2017

(54) BLANK MATERIAL TO BE CUT FOR DENTISTRY, METAL POWDER FOR POWDER METALLURGY, METAL FRAME FOR PORCELAIN FUSING FOR DENTISTRY, AND DENTAL PROSTHESIS

(71) Applicant: Seiko Epson Corporation, Tokyo (JP)

(72) Inventors: Hidefumi Nakamura, Hachinohe (JP); Takayuki Tamura, Hachinohe (JP)

(73) Assignee: Seiko Epson Corporation (JP)

( * ) Notice: Subject to any disclaimer, the term of this patent is extended or adjusted under 35 U.S.C. 154(b) by 201 days.

(21) Appl. No.: 14/609,861

(22) Filed: Jan. 30, 2015

(65) Prior Publication Data
US 2015/0216636 A1    Aug. 6, 2015

(30) Foreign Application Priority Data

Jan. 31, 2014   (JP) .................. 2014-018073
Oct. 9, 2014    (JP) .................. 2014-208338

(51) Int. Cl.
*A61C 13/00*     (2006.01)
*A61C 13/083*    (2006.01)
(Continued)

(52) U.S. Cl.
CPC ...... *A61C 13/0022* (2013.01); *A61C 13/0004* (2013.01); *A61C 13/0006* (2013.01); *A61C 13/0835* (2013.01); *C22C 1/0433* (2013.01); *C22C 19/07* (2013.01); *B22F 3/15* (2013.01); *B22F 7/06* (2013.01); *Y10T 428/12229* (2015.01)

(58) Field of Classification Search
CPC ... A61C 13/00; A61C 13/0022; A61C 13/085; A61C 13/0004; A61C 13/0006; B22F 3/22; B22F 3/15; B22F 7/06; B22F 3/12; B22F 1/00; B22F 3/24; C22C 1/0433; C22C 19/07; Y10T 428/12229
See application file for complete search history.

(56) References Cited

U.S. PATENT DOCUMENTS 5,462,575 A    10/1995  Del Corso
6,896,846 B1    5/2005  Varma et al.
(Continued)

FOREIGN PATENT DOCUMENTS

GB          943190 A  * 12/1963   ......... A61C 13/0835
JP      11-001738 A      1/1999
(Continued)

OTHER PUBLICATIONS

Extended European Search Report for European Patent Application No. 15153311.4 dated Jun. 30, 2015 (8 pages).

*Primary Examiner* — Nicholas Lucchesi
(74) *Attorney, Agent, or Firm* — Harness, Dickey & Pierce, P.L.C.

(57) ABSTRACT

A blank material to be cut for dentistry includes: Co as a main component; Cr at a ratio equal to or higher than 26 mass % and equal to or less than 35 mass %; Mo at a ratio equal to or higher than 5 mass % and equal to or less than 12 mass %; Si at a ratio equal to or higher than 0.3 mass % and equal to or less than 2.0 mass %; and N at a ratio equal to or higher than 0.09 mass % and equal to or less than 0.5 mass %. The blank material is formed of a sintered body of a metal powder.

16 Claims, 8 Drawing Sheets

(51) Int. Cl.
*C22C 1/04* (2006.01)
*C22C 19/07* (2006.01)
*B22F 3/15* (2006.01)
*B22F 7/06* (2006.01)

(56) References Cited

U.S. PATENT DOCUMENTS

2008/0232998 A1* 9/2008 Prasad ............... A61C 13/0003 420/436
2009/0298016 A1 12/2009 Chu et al.
2011/0189440 A1* 8/2011 Appleby ................ B22C 9/04 428/156
2011/0275031 A1* 11/2011 Jana ................... A61C 13/0006 433/172
2011/0314965 A1 12/2011 Nakamura
2012/0114516 A1* 5/2012 Hachenberg ....... A61C 13/0022 419/25
2012/0174404 A1* 7/2012 Wolz .................. A61C 13/0003 29/896.1
2012/0244035 A1* 9/2012 Cascone ................ C22C 30/00 420/583
2013/0224688 A1* 8/2013 Mayr ....................... A61C 5/10 433/200.1
2013/0277874 A1* 10/2013 Johnson ............. A61C 13/0004 264/16
2015/0093721 A1* 4/2015 Nakamura ......... A61C 13/0022 433/206

FOREIGN PATENT DOCUMENTS

| JP | 2006-328475 A | 12/2006 |
| JP | 2007-215854 A | 8/2007 |
| JP | 2009-138259 A | 6/2009 |
| JP | 2010-150587 A | 7/2010 |
| JP | 2012-007205 A | 1/2012 |
| JP | 2012-087415 A | 5/2012 |
| JP | 2012-087416 A | 5/2012 |

* cited by examiner

BLANK MATERIAL TO BE CUT FOR DENTISTRY, METAL POWDER FOR POWDER METALLURGY, METAL FRAME FOR PORCELAIN FUSING FOR DENTISTRY, AND DENTAL PROSTHESIS

CROSS-REFERENCE TO RELATED APPLICATIONS

This application claims priority to Japanese Patent Application No. 2014-018073 filed on Jan. 31, 2014, Japanese Patent Application No. 2014-208338 filed on Oct. 9, 2014. The entire disclosures of Japanese Patent Application Nos. 2014-018073, 2014-208338 are hereby incorporated herein by reference.

BACKGROUND

1. Technical Field

The present invention relates to a blank material to be cut for dentistry, a metal powder for powder metallurgy, a metal frame for porcelain fusing for dentistry, and a dental prosthesis.

2. Related Art

In order to replace crown defects or tooth defects during a dental treatment, crowns, bridges, or artificial teeth are widely used. Among these, from the viewpoint of aesthetics and functionality, a dental prosthesis in which a ceramic material called porcelain is fused to the surface of a metal frame is used.

In JP-A-11-1738, a precious metal-based alloy for a metal frame in which metal elements such as Sn, Ga, and In are added to metal elements such as Au, Pd, Cu, Ir, and Ag is disclosed. This alloy can be molded into a desired shape by a casting method. Therefore, by fusing crown restoration porcelain to the surface of the metal frame made of the alloy, a dental prosthesis having excellent aesthetics can be obtained.

Recently, a method of forming a metal frame on the basis of shape data obtained by measuring the three-dimensional shape of an affected area has become more common. The mechanism used in this method is called a dental CAD/CAM system. CAD (computer aided design) is a system which acquires the three-dimensional shape of an affected area using a 3D scanner or the like and digitizes the shape. In addition, CAM (computer aided manufacturing) is a system which cuts a processing object on the basis of the numerical data generated by CAD to be machined into a frame having an appropriate shape for the affected area. The dental CAD/CAM system which has the combined systems can easily realize high dimensional accuracy that does not intricately depend on the skill of a dental technician according to the related art and thus can efficiently form a metal frame having excellent compatibility with the affected area. Accordingly, further spreading of the system is expected (for example, refer to JP-A-2007-215854).

The processing object provided for the dental CAD/CAM system is generally called a "blank" or "blank material". The blank material requires machinability in addition to properties desired for a metal frame including aesthetics, compatibility with a living body, chemical stability, and wear resistance. Machinability is the ability to be properly cut, and by using a blank material with good machinability, a metal frame which is accurately reproduced in a desired shape can be efficiently machined by the CAM on the basis of numerical data generated by CAD.

The alloy described in JP-A-11-1738 is an alloy appropriate for the casting method but has a problem of degraded machinability. In a case where the machinability of the blank material is poor, the intended processing cannot be performed, and a difference occurs between a shape after the processing is complete and the desired shape. As a result, effort for secondary processing to modify the as-processed shape is needed. In addition, since compatibility with the affected area is low, there is a problem in that a patient may sense the incompatibility.

SUMMARY

An advantage of some aspects of the invention is to provide a blank material to be cut for dentistry having excellent machinability, a metal powder for powder metallurgy with which the blank material to be cut can be manufactured, a metal frame for porcelain fusing for dentistry having excellent adhesion to porcelain, and a dental prosthesis having high reliability.

An aspect of the invention is directed to a blank material to be cut for dentistry including: Co as a main component; Cr at a ratio of equal to or higher than 26 mass % and equal to or less than 35 mass %; Mo at a ratio of equal to or higher than 5 mass % and equal to or less than 12 mass %; Si at a ratio of equal to or higher than 0.3 mass % and equal to or less than 2.0 mass %; and N at a ratio of equal to or higher than 0.09 mass % and equal to or less than 0.5 mass %, in which the blank material is formed of a sintered body of a metal powder.

With this configuration, a structure unique to the sintered body is achieved, and thus the blank material to be cut for dentistry having excellent machinability is obtained.

In the blank material to be cut for dentistry according to the aspect of the invention, when a position of a cross-section of the blank material to be cut at a depth of 0.3 mm from a surface is referred to as a surface layer portion and a position of the cross-section at a depth of 5 mm from the surface is referred to as an inner layer portion, it is preferable that a concentration of N in the inner layer portion is equal to or higher than 50% and equal to or less than 200% of a concentration of N in the surface layer portion.

With this configuration, the properties of the inner layer portion and the surface layer portion are similar to each other, and thus when cutting work is performed on the blank material to be cut for dentistry, a change in machinability during the cutting is suppressed. Therefore, the dimensional accuracy of a metal frame machined from the blank material is less likely to be degraded. In addition, the metal frame is suppressed from partially varying in mechanical properties.

In the blank material to be cut for dentistry according to the aspect of the invention, when a position of a cross-section of the blank material to be cut at a depth of 0.3 mm from a surface is referred to as a surface layer portion and a position of the cross-section at a depth of 5 mm from the surface is referred to as an inner layer portion, it is preferable that a Vickers hardness in the inner layer portion is equal to or higher than 67% and equal to or less than 150% of a Vickers hardness in the surface layer portion.

With this configuration, the hardness of the inner layer portion and the hardness of the surface layer portion are similar to each other, and thus when cutting work is performed on the blank material to be cut for dentistry, a change in machinability during the cutting is suppressed. Therefore, the dimensional accuracy of a metal frame machined from the blank material is less likely to be degraded.

In the blank material to be cut for dentistry according to the aspect of the invention, it is preferable that the Vickers hardness of the inner layer portion is equal to or higher than 200 and equal to or less than 480.

With this configuration, a blank material from which a metal frame having sufficient deformation resistance even against masticatory (chewing) force can be manufactured is obtained. In addition, since cutting resistance is relatively reduced, machinability is excellent, and thus a blank material which can be efficiently machined into a metal frame having a desired shape and dimensions is obtained.

In the blank material to be cut for dentistry according to the aspect of the invention, it is preferable that a ratio of the N content to the Si content is equal to or higher than 0.1 and equal to or less than 0.8.

With this configuration, high mechanical properties and high machinability can be allowed to coexist with each other. That is, machinability is enhanced by adding a certain amount of Si, however, there is concern that the mechanical properties of the blank material may be degraded when the amount of Si being added is too high. Here, when N is added at a ratio in the above range, high machinability caused by the addition of Si and the effect caused by the addition of N can be exhibited without cancelling each other. Therefore, a synergistic increase in machinability can be achieved. Furthermore, it is thought that the strain of a crystal structure caused by the solutionizing of Si is suppressed by the solutionizing of N. Therefore, it is thought that the degradation in mechanical properties is prevented. In addition, when Si is added, strain occurs in the crystal structure. However, in this state, a high degree of hysteresis easily occurs in the behavior of thermal expansion and thermal contraction. When there is a high degree of hysteresis in the behavior of thermal expansion and thermal contraction, there is concern that the thermal properties of the blank material may change with time. Meanwhile, since N is added at the above-described ratio, N infiltrates the crystal structure and is solutionized, thereby suppressing the strain of the crystal structure. As a result, hysteresis in the behavior of thermal expansion and thermal contraction is suppressed, and thus the stability of the thermal properties of the blank material can be achieved.

In the blank material to be cut for dentistry according to the aspect of the invention, it is preferable that a portion of the Si is contained as a silicon oxide, and a ratio of Si contained as the silicon oxide to the Si mentioned above is equal to or higher than 10 mass % and equal to or less than 90 mass %.

With this configuration, effects such as high machinability, high mechanical properties of the metal frame, and high adhesion of porcelain are caused. In addition, since a certain amount of the silicon oxide is present, the amount of oxides of transition metal elements such as Co, Cr, and Mo contained in the blank material can be sufficiently suppressed. As a result, the realization of a dental prosthesis having higher reliability is achieved.

In the blank material to be cut for dentistry according to the aspect of the invention, it is preferable that the silicon oxide segregates to a grain boundary of the sintered body.

With this configuration, the enlargement of metal crystals is more reliably suppressed, thereby obtaining a blank material which can be machined into a metal frame having excellent mechanical properties. Furthermore, precipitates of the silicon oxide segregated to the grain boundaries naturally maintain an appropriate distance, and thus the precipitates of the silicon oxide can be more uniformly dispersed in the blank material. As a result, a more homogeneous blank material can be obtained.

In the blank material to be cut for dentistry according to the aspect of the invention, in an X-ray diffraction pattern obtained by X-ray diffractometry using CuKα radiation, when a height of a highest peak among peaks caused by Co identified on the basis of an ICDD card is assumed to be 1, it is preferable that a ratio of a height of a highest peak among peaks caused by $Co_3Mo$ identified on the basis of the ICDD card is equal to or higher than 0.01 and equal to or less than 0.5.

With this configuration, a reduction in the hardness of the metal frame is prevented. Accordingly, a dental prosthesis which is less likely to be deformed by masticatory force can be manufactured, and a blank material in which reductions in tensile strength, proof stress, and elongation are suppressed is obtained.

In the blank material to be cut for dentistry according to the aspect of the invention, it is preferable that the blank material to be cut for dentistry has a 0.2% proof stress of equal to or higher than 450 MPa, an elongation of equal to or higher than 2%, and a Young's modulus of equal to or higher than 150 GPa.

With this configuration, a blank material from which a metal frame having excellent durability can be manufactured is obtained.

Another aspect of the invention is directed to a metal powder for powder metallurgy including: Co as a main component; Cr at a ratio of equal to or higher than 26 mass % and equal to or less than 35 mass %; Mo at a ratio of equal to or higher than 5 mass % and equal to or less than 12 mass %; Si at a ratio of equal to or higher than 0.3 mass % and equal to or less than 2.0 mass %; and N at a ratio of equal to or higher than 0.09 mass % and equal to or less than 0.5 mass %, in which the metal powder is used to manufacture a blank material to be cut for dentistry.

With this configuration, a metal powder for powder metallurgy from which a blank material to be cut for dentistry having excellent machinability can be manufactured is obtained.

Still another aspect of the invention is directed to a metal frame for porcelain fusing for dentistry including: Co as a main component; Cr at a ratio of equal to or higher than 26 mass % and equal to or less than 35 mass %; Mo at a ratio of equal to or higher than 5 mass % and equal to or less than 12 mass %; Si at a ratio of equal to or higher than 0.3 mass % and equal to or less than 2.0 mass %; and N at a ratio of equal to or higher than 0.09 mass % and equal to or less than 0.5 mass %, in which the metal frame is machined from a blank material to be cut for dentistry which is formed of a sintered body of a metal powder.

With this configuration, a metal frame for porcelain fusing for dentistry having excellent adhesion of porcelain is obtained.

Yet another aspect of the invention is directed to a dental prosthesis including: the metal frame for porcelain fusing for dentistry according to the aspect; and a porcelain layer provided on a surface of the metal frame for porcelain fusing for dentistry.

With this configuration, a dental prosthesis having high reliability in which the metal frame for porcelain fusing for dentistry and the porcelain layer come into close contact with each other is obtained.

In the dental prosthesis according to the aspect of the invention, it is preferable that the porcelain layer contain alumina, and a mullite phase is further provided between the metal frame for porcelain fusing for dentistry and the porcelain layer.

With this configuration, the porcelain layer and the metal frame come in close contact with each other via the mullite phase, so that the porcelain layer is less likely to be exfoliated and a dental prosthesis having high reliability is obtained. In addition, it is thought that as the mullite phase is generated, wettability of a ceramic material for the metal frame is enhanced during a fusing treatment. Therefore, from this point of view, the adhesion of the porcelain layer is thought to be increased.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

Hereinafter, a blank material to be cut for dentistry, a metal powder for powder metallurgy, a metal frame for porcelain fusing for dentistry, and a dental prosthesis according to the invention will be described in detail on the basis of preferred exemplary embodiments illustrated in the accompanying drawings.

Blank Material to be Cut for Dentistry

First, an embodiment of the blank material to be cut for dentistry according to the invention will be described.

Figure 1:
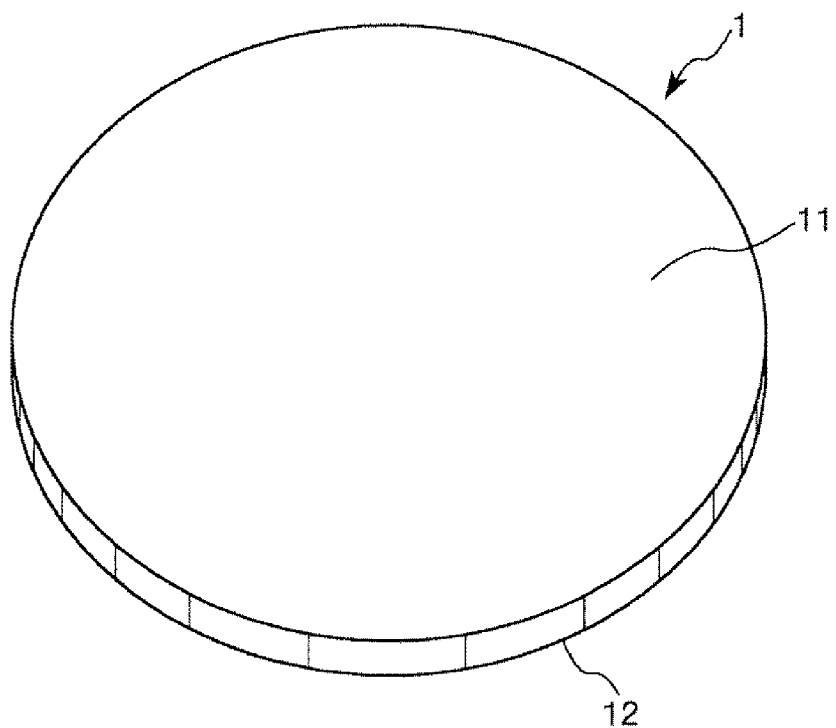
FIG. 1 is a perspective view illustrating an embodiment of a blank material to be cut for dentistry according to the invention.
Figure 2:
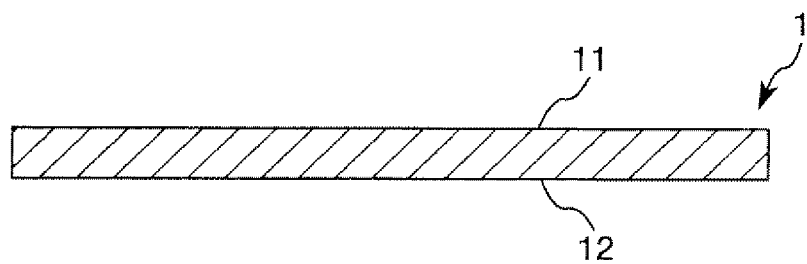
FIG. 2 is a longitudinal cross-sectional view of the blank material to be cut for dentistry illustrated in FIG. 1.

FIG. 1 is a perspective view illustrating the embodiment of the blank material to be cut for dentistry according to the invention, and FIG. 2 is a longitudinal cross-sectional view of the blank material to be cut for dentistry illustrated in FIG. 1.

A blank material to be cut for dentistry 1 (hereinafter, also referred to as a "blank material 1" for short) illustrated in FIG. 1 is a member used to machine a metal dental component having a desired shape which is provided for cutting. The blank material to be cut for dentistry includes a "CAD/CAM blank material" and a "dental mill blank" which are provided for the dental CAD/CAM system as described above to be processed by the CAM. The dental metal component is not particularly limited as long as it is a metal component retained temporarily or semi-permanently in the mouth and in the following description, a case of machining a metal frame will be described.

The blank material 1 illustrated in FIGS. 1 and 2 has a disk shape, that is, a columnar shape having a smaller height than its diameter, and an upper surface 11 and a lower surface 12 of the blank material 1 are flat surfaces that are parallel to each other. The shape of the blank material to be cut for dentistry according to the invention is not limited to the disk shape and may be any shape. For example, shapes such as a rectangular parallelepiped shape, a cubic shape, a spherical shape, and a polygonal column shape may be employed.

The diameters of the upper surface 11 and the lower surface 12 of the blank material 1 illustrated in FIGS. 1 and 2 are not particularly limited and may be, as an example, about equal to or greater than 30 mm and equal to or less than 500 mm. In addition, the thickness of the blank material 1 is also set as desired depending on the diameter, and as an example, is about equal to or greater than 3 mm and equal to or less than 50 mm, and is preferably about equal to or greater than 10 mm and equal to or less than 40 mm.

The blank material 1 is made of a Co—Cr—Mo—Si—N-based alloy.

Specifically, the alloy contained in the blank material 1 contains Co as a main component, Cr at a ratio of equal to or higher than 26 mass % and equal to or less than 35 mass %, Mo at a ratio of equal to or higher than 5 mass % and equal to or less than 12 mass %, Si at a ratio of equal to or higher than 0.3 mass % and equal to or less than 2.0 mass %, and N at a ratio of equal to or higher than 0.09 mass % and equal to or less than 0.5 mass %.

The blank material 1 made of the alloy has compatibility with a living body and chemical stability and also has excellent machinability. Therefore, when a metal frame is machined by cutting the blank material 1, cut waste is smoothly discharged, and the roughness of the cut surface is sufficiently low, thereby continuously performing cutting stably over a long period of time is possible. In addition, defects and wear of a cutting tool can be minimized. As a result, the cutting amount during the cutting is achieved as desired, and thus the machined metal frame can be provided having dimensions and shapes as designed.

In addition, this metal frame can be attached to a patient with low incompatibility with an affected area and thus the burden on the patient can be minimized. In addition, high adhesion and high aesthetics can be realized when porcelain is fused to the metal frame.

Here, among the elements contained in the alloy, Co (cobalt) is the main component of the alloy contained in the blank material 1 and greatly affects the basic properties of the blank material 1.

The Co content is set to be highest among the elements contained in the alloy, and specifically, is preferably equal to or higher than 50 mass % and equal to or less than 67.5 mass % and more preferably equal to or higher than 55 mass % and equal to or less than 67 mass %.

Cr (chromium) mainly acts to enhance the corrosion resistance of the blank material 1. It is thought that this is because a passive film ($Cr_2O_3$ and the like) is more likely to be formed in the alloy due to the addition of Cr and thus chemical stability is enhanced. Due to the enhancement of the corrosion resistance, for example, an effect of metal ions being less likely to be eluted even in the case of coming into contact with a body fluid is expected. Therefore, it can be said that the blank material 1 made of the alloy containing Cr can be machined into a metal frame having excellent compatibility with a living body. In addition, since Cr is used together with Co, Mo, and Si, the mechanical properties of the metal frame can be enhanced.

The Cr content in the alloy contained in the blank material 1 is equal to or higher than 26 mass % and equal to or less than 35 mass %. When the Cr content is less than the lower limit, the corrosion resistance of the metal frame machined from the blank material 1 is degraded. Therefore, in a case where the metal frame comes into contact with a body fluid for a long period of time, there is concern that metal ions may be eluted. On the other hand, when the Cr content is higher than the upper limit, the amount of Cr with respect to Mo and Si is relatively too high and thus there is concern that machinability may be degraded. Furthermore, the balance between Co, Mo and Si may be ruined, resulting in the degradation of mechanical properties.

In addition, the Cr content is preferably equal to or higher than 27 mass % and equal to or less than 34 mass % and more preferably equal to or higher than 28 mass % and equal to or less than 33 mass %.

Mo (molybdenum) mainly acts to increase the corrosion resistance of the blank material 1. That is, corrosion resistance due to the addition of Cr can be further strengthened by the addition of Mo. It is thought that this is because a passive film containing chromium oxide as the main material is further densified by adding Mo. Therefore, the alloy to which Mo is added causes metal ions to be even less likely to be eluted, contributing to the realization of a metal frame having particularly high compatibility with a living body.

The Mo content in the alloy contained in the blank material 1 is equal to or higher than 5 mass % and equal to or less than 12 mass %. When the Mo content is less than the lower limit, there is concern that the corrosion resistance of the metal frame machined from the blank material 1 may become insufficient. On the other hand, when the Mo content is higher than the upper limit, the amount of Mo with respect to Cr and Si is relatively too high and thus there is concern that machinability may be degraded.

In addition, the Mo content is preferably equal to or higher than 5.5 mass % and equal to or less than 11 mass % and more preferably equal to or higher than 6 mass % and equal to or less than 9 mass %.

In addition, Si (silicon) mainly acts to enhance the machinability of the blank material 1. Due to the addition of Si, silicon oxides formed by the oxidation of a portion of Si are generated in the blank material 1. As the silicon oxides, there are SiO, $SiO_2$, and the like. When the silicon oxide is generated in the blank material 1, metal crystals are separated at the site. Therefore, it is thought that the structure of the blank material 1 is locally discontinuous in the vicinity of silicon oxide. When the blank material 1 in this state is cut by using a cutting tool, it is thought that when cut waste generated from the tip end of the cutting tool becomes separated from the body of the blank material 1, the silicon oxide acts as a starting point and the cut waste is easily separated. As a result, it is thought that cutting resistance is reduced and thus the machinability of the blank material 1 is increased.

Furthermore, Si also acts to increase the mechanical properties of the metal frame machined from the blank material 1. The above-mentioned silicon oxides suppress the metal crystals from being significantly enlarged when the metal crystals grow during the manufacturing of the blank material 1. Therefore, in the alloy to which Si is added, the grain sizes of the metal crystals are suppressed to be small, thereby further increasing the mechanical properties of the metal frame.

Accordingly, by adding Si, the machinability of the blank material 1 and the mechanical properties of the metal frame machined from the blank material 1 can be allowed to coexist with each other.

Furthermore, since Si is added, the adhesion of the porcelain to the metal frame machined from the blank material 1 is enhanced. Therefore, when a porcelain layer is provided to cover the surface of the metal frame, the exfoliation of the porcelain layer is suppressed, thereby obtaining a dental prosthesis having high reliability.

In addition, in order to obtain the above-described effect, the Si content is desirably set to be equal to or higher than 0.3 mass % and equal to or less than 2.0 mass %. When the Si content is less than the lower limit, the amount of the silicon oxides is small, resulting in an increase in the cutting resistance. Therefore, the machinability of the blank material 1 is degraded and the metal crystals are likely to be enlarged during the manufacturing of the blank material 1. Accordingly, there is a high possibility that the mechanical properties of the metal frame machined from the blank material 1 may be degraded. In addition, since the adhesion of the porcelain to the metal frame becomes insufficient, problems such as the exfoliation of the porcelain layer may easily occur in the dental prosthesis. On the other hand, when the Si content is higher than the upper limit, the amount of the silicon oxide present in the blank material 1 is too large, and thus an area in which the silicon oxide is spatially continuously distributed is easily generated. In this area, the structure of the blank material 1 is discontinuous in a certain size, and thus the area may become a starting point of a fracture when an external force is applied to the blank material 1. Therefore, the mechanical properties of the blank material 1 are degraded.

In addition, the Si content is preferably equal to or higher than 0.5 mass % and equal to or less than 1.0 mass %, and more preferably equal to or higher than 0.6 mass % and equal to or less than 0.9 mass %.

It is preferable that a portion of Si be present in a silicon oxide state as described above. However, regarding the amount of Si being present, the ratio of Si contained as the silicon oxides to the total amount of Si is preferably equal to or higher than 10 mass % and equal to or less than 90 mass %, more preferably equal to or higher than 20 mass % and equal to or less than 80 mass %, even more preferably equal to or higher than 30 mass % and equal to or less than 70 mass %, and particularly preferably equal to or higher than 35 mass % and equal to or less than 65 mass %. By setting the ratio of Si contained as the silicon oxide to the total amount of Si to be in the above range, the effects of the blank material 1 as described above, such as the machinability, the mechanical properties of the metal frame, and the adhesion of the porcelain, are caused. In addition, since a certain amount of the silicon oxide is present, the amount of oxides of transition metal elements such as Co, Cr, and Mo contained in the blank material 1 can be sufficiently suppressed. It is thought that this is because Si is more easily oxidized than Co, Cr, and Mo, a reduction reaction occurs as Si gains oxygen that is bonded to the transition metal elements, and the fact that not a total amount of Si is the silicon oxide is the same as that the transition metal elements sufficiently undergo the reduction reaction. Therefore, by setting the ratio of Si contained as the silicon oxide to Si to be in the above range, the effects of the blank material 1 as described above, such as high machinability, high mechanical properties of the metal frame, and high adhesion of the porcelain, are suppressed from being impeded by the oxides of Co, Cr, or Mo. As a result, the realization of a dental prosthesis having higher reliability is achieved.

In addition, by setting the ratio of Si contained as the silicon oxide to Si to be in the above range, the blank material 1 can be provided with a desired hardness. That is, it is thought that since a certain amount of Si that is not contained in the silicon oxides is present, Si and at least one of Co, Cr, and Mo produce hard intermetallic compounds, and this results in an increase in the hardness of the blank material 1. As the hardness of the blank material 1 is increased, the hardness of the metal frame machined from the blank material 1 is also increased. Therefore, the dental prosthesis including the metal frame is less likely to be deformed by masticatory force after being mounted on the affected area, thereby increasing reliability. In other words, by adding Si, significant growth of the metal crystals is impeded. From this point of view, although the hardness of the blank material 1 tends to decrease, a significant reduction in the hardness is suppressed by the portion of Si that produces intermetallic compounds, thereby ensuring reliability in the dental prosthesis.

The intermetallic compounds are not particularly limited, and examples thereof include $CoSi_2$, $Cr_3Si$, $MoSi_2$, and $Mo_5Si_3$.

In addition, the ratio of Si contained as the silicon oxides to the total amount of Si may be obtained by using a weight method and an ICP emission spectrometry.

In addition, in consideration of a precipitation amount of the intermetallic compounds, the ratio of the Si content to the Mo content (Si/Mo) is preferably equal to or higher than 0.05 and equal to or less than 0.2 in terms of mass ratio and more preferably equal to or higher than 0.08 and equal to or less than 0.15. Accordingly, the blank material 1 from which a dental prosthesis having high reliability can be manufactured while suppressing a significant degradation in the machinability of the blank material 1 is obtained.

The silicon oxides may be distributed at any position and are preferably distributed to segregate to a grain boundary (the interface between metal crystals). As the silicon oxides segregate to such a position, the enlargement of the metal crystals is more reliably suppressed, thereby obtaining the blank material 1 which can be machined into a metal frame having excellent mechanical properties. Furthermore, precipitates of the silicon oxide segregated to the grain boundaries naturally maintain an appropriate distance, and thus the precipitates of the silicon oxide can be more uniformly dispersed in the blank material 1. As a result, a more homogeneous blank material 1 can be obtained.

Even in a case where the blank material 1 is machined into a plurality of metal frames, the blank material 1 contributes to minimizing individual differences in properties between the metal frames.

In addition, the sizes, the distribution, and the like of the precipitates of the segregated silicon oxides can be specified by qualitative analysis of the surface. Specifically, in a composition image of Si obtained by an electron probe microanalyzer (EPMA), the average diameter of regions where Si is segregated is preferably equal to or greater than 0.1 μm and equal to or less than 10 μm and more preferably equal to or greater than 0.3 μm and equal to or less than 8 μm. When the average diameter of the regions where Si is segregated is in the above range, the size of the precipitates of the silicon oxide is optimized to exhibit the effects described above. That is, when the average diameter of the regions where Si is segregated is less than the lower limit, the precipitates of the silicon oxide are not segregated into sufficient sizes, and there is concern that the above-described effects may not be sufficiently obtained. On the other hand, when the average diameter of the regions where Si is segregated is higher than the upper limit, there is concern that the mechanical properties of the blank material 1 may be degraded.

In addition, the average diameter of the regions where Si is segregated may be obtained from the average value of diameters of circles having the same areas as those of the regions where Si is segregated (projected area equivalent circle diameter). In addition, the average diameter of the regions where Si is segregated is obtained as an average value of measurement values of 100 or more regions where Si is segregated.

Figure 3:
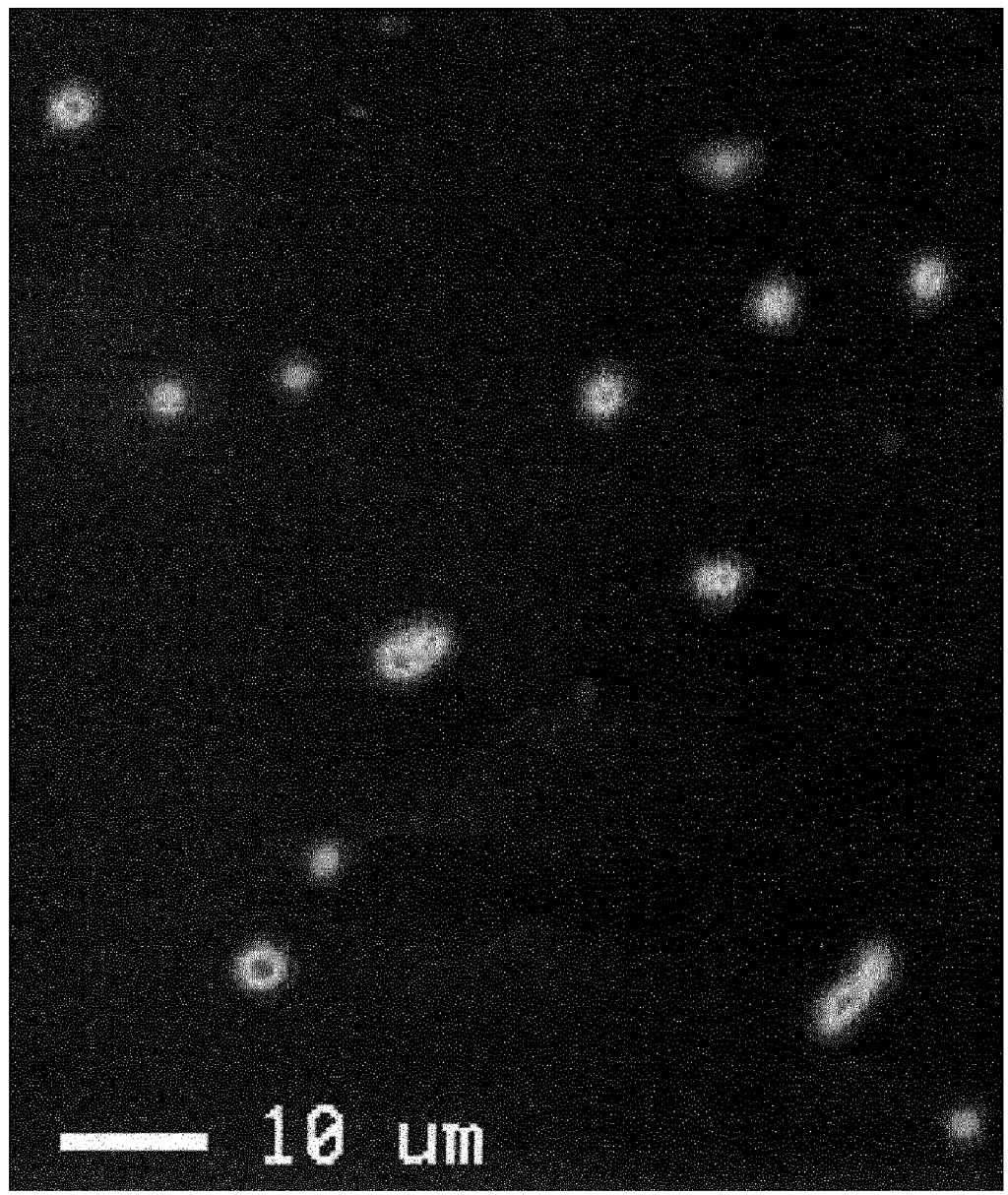
FIG. 3 is an example of a composition image of Si of the blank material to be cut for dentistry according to the invention, which is obtained by an electron probe microanalyzer.

FIG. 3 is an example of the composition image of Si of the blank material to be cut for dentistry according to the invention, which is obtained by the electron probe microanalyzer.

As is apparent from the composition image, it is clear that Si locally agglomerates in the blank material to be cut for dentistry according to the invention and the agglomerates (light color portions of FIG. 3) are dispersed. It is thought that this indicates that silicon oxides segregate to the grain boundaries.

In addition, the blank material 1 includes a first phase mainly containing Co and a second phase mainly containing $Co_3Mo$. Since the second phase is included among these, the metal frame can be provided with a desired hardness like the intermetallic compounds containing Si described above. Accordingly, the blank material 1 which is useful from the viewpoint of enhancing the reliability of the dental prosthesis is obtained. On the other hand, in a case where the second phase is excessively included, the second phase easily segregates and results in the degradation in mechanical properties such as tensile strength, proof stress, and elongation.

Therefore, it is preferable that the first phase and the second phase be included at a desired ratio from the above viewpoints. Specifically, a crystal structure analysis is performed on the blank material 1 according to X-ray diffractometry using CuKα radiation, and when the height of the highest peak among the peaks caused by Co is assumed to be 1, the height of the highest peak among the peaks caused by $Co_3Mo$ is preferably equal to or higher than 0.01 and equal to or less than 0.5, and more preferably equal to or higher than 0.02 and equal to or less than 0.4.

In addition, when the ratio of the height of the peak of $Co_3Mo$ is less than the lower limit when the height of the peak of Co is assumed to be 1, the ratio of $Co_3Mo$ with respect to Co in the blank material 1 decreases. Therefore, the hardness of the metal frame is reduced, and there is concern that the dental prosthesis may be easily deformed by masticatory force. On the other hand, when the ratio of the height of the peak of $Co_3Mo$ is higher than the upper limit, the amount of $Co_3Mo$ present becomes excessive, and thus $Co_3Mo$ is likely to segregate. Accordingly, there is concern that tensile strength and proof stress may be reduced and elongation may also be reduced.

In addition, the CuKα radiation is a characteristic X-ray at an energy of 8.048 keV.

When the peak caused by Co is to be identified, the peak is identified on the basis of the database for Co of the International Centre for Diffraction Data (ICDD) card. Similarly, when the peak caused by $Co_3Mo$ is to be identified, the peak is identified on the basis of the database for $Co_3Mo$ of the ICDD card.

In addition, the ratio of $Co_3Mo$ present in the blank material 1 is preferably equal to or higher than 0.01 mass % and equal to or less than 10 mass %, and more preferably equal to or higher than 0.05 mass % and equal to or less than 5 mass %. Accordingly, a metal frame having desired hardness, tensile strength, proof stress, and elongation is obtained, and thus a dental prosthesis which is less likely to be deformed by masticatory force is obtained.

The presence ratio is obtained by quantifying the ratio of $Co_3Mo$ being present from the results of the crystal structure analysis.

Furthermore, N (nitrogen) mainly acts to enhance the mechanical properties of the blank material 1. Since N is an austenitizing element, N acts to accelerate the austenitization of the crystal structure of the blank material 1, suppress an increase in the hardness of the blank material 1, and increase toughness.

In addition, by including N, the generation of a dendritic phase in the blank material 1 formed of a sintered body of a metal powder is suppressed, and thus the dendritic phase content is very low. From this point of view, an increase in the hardness of the blank material 1 is suppressed and toughness can be increased.

The blank material 1 containing N has a desired hardness, high toughness, and a low dendritic phase content as described above. Therefore, the blank material 1 has high machinability, and thus a metal frame having high dimensional accuracy can be efficiently machined.

Here, the dendritic phase is a crystal structure which is dendritically grown. However, when a large amount of the dendritic phase is contained, the machinability of the blank material 1 is degraded. Therefore, reducing the dendritic phase content is effective in increasing the machinability of the blank material 1. Specifically, the area ratio of the dendritic phase to an observation image obtained by observing the blank material 1 with a scanning electron microscope is preferably equal to or less than 20% and more preferably equal to or less than 10%. The blank material 1 which satisfies such conditions has particularly excellent mechanical properties and machinability.

In addition, the blank material 1 is formed of the sintered body of the metal powder as described above. Since the volume of each particle in the metal powder is very small, the metal powder has a high cooling rate and cooling uniformity is also high. Therefore, in the blank material 1 formed of the sintered body of the metal powder, the generation of the dendritic phase is suppressed. On the other hand, in an existing method such as casting, molten metal is poured into a mold having the shape of the blank material and thus the volume to be cooled is very large. Therefore, the cooling rate is low and cooling uniformity is also low. As a result, it is thought that a large amount of the dendritic phase is generated in the blank material manufactured in the above-described method.

In addition, the area ratio mentioned above is calculated as the ratio of an area occupied by the dendritic phase to the area of the observation image, and one side of the observation image is set to be about equal to or greater than 50 μm and equal to or smaller than 1000 μm.

In order to obtain the above-described effects, the N content is desirably set to be equal to or higher than 0.09 mass % and equal to or less than 0.5 mass %. When the N content is less than the lower limit, the austenitization of the crystal structure of the blank material 1 is insufficiently achieved, and thus the hardness of the blank material 1 greatly increases, resulting in the degradation in toughness. Therefore, the machinability and the mechanical properties of the blank material 1 are degraded. It is thought that this is because a large amount of hcp structures (ε phase) are precipitated in the blank material 1 in addition to the austenite phase (γ phase). On the other hand, when the N content is higher than the upper limit, a large amount of various types of nitrides are generated and a composition which is less likely to be sintered is formed. Therefore, the sintering density of the blank material 1 is reduced, resulting in the degradation in mechanical properties. Examples of the generated nitrides include $Cr_2N$ and the like. When such nitrides are precipitated, hardness is also increased, and thus toughness is also reduced.

The N content is preferably equal to or higher than 0.12 mass % and equal to or less than 0.4 mass %, more preferably equal to or higher than 0.14 mass % and equal to or less than 0.25 mass %, and even more preferably equal to or higher than 0.15 mass % and equal to or less than 0.22 mass %.

Particularly in a range of equal to or higher than 0.15 mass % and equal to or less than 0.22 mass %, the austenite phase is particularly dominant, and thus a significant reduction in hardness and significant enhancement of toughness are recognized. When the blank material 1 at this time is provided for the crystal structure analysis according to the X-ray diffractometry using the CrKα radiation, a main peak caused by the austenite phase is very strongly recognized, and the heights of the peaks caused by the hcp structures and the other peaks are equal to or less than 5% of the height of the main peak. From this, it is understood that the austenite phase is dominant.

The ratio (N/Si) of the N content to the Si content is preferably equal to or higher than 0.1 and equal to or less than 0.8 in terms of mass ratio and more preferably equal to or higher than 0.2 and equal to or less than 0.6. Accordingly, high mechanical properties and high machinability can be allowed to coexist with each other. That is, machinability is enhanced as described above by adding a certain amount of Si while there is concern that the mechanical properties of the blank material 1 may be degraded when the amount of Si being added is too high. Here, when N is added at a ratio in the above range, high machinability caused by the addition of Si and the above-described effects caused by the addition of N can be exhibited without cancelling each other out. Therefore, a synergistic increase in machinability can be achieved. It is thought that this is because metal elements such as Si and Co generate substitutional solid solutions while metal elements such as N and Co generate interstitial solid solutions, and thus the solid solutions coexist with each other. Furthermore, it is thought that the strain of the crystal structure caused by the solutionizing of Si is suppressed by the solutionizing of N. Therefore, it is thought that the degradation in mechanical properties is prevented.

In addition, when Si is added, strain occurs in the crystal structure as described above. However, in this state, a high degree of hysteresis easily occurs in the behavior of thermal expansion and thermal contraction. When there is a high degree of hysteresis in the behavior of thermal expansion and thermal contraction, there is concern that the thermal properties of the blank material 1 may change with time.

Meanwhile, since N is added at the above-described ratio, N infiltrates into the crystal structure and is solutionized, thereby suppressing the strain of the crystal structure. As a result, hysteresis in the behavior of thermal expansion and thermal contraction is suppressed, and thus the stability of the thermal properties of the blank material 1 can be achieved.

For the above reasons, Si and N are added as desired. Accordingly, the machinability of the blank material 1 is enhanced and the stability of mechanical properties and the stability of thermal properties can be achieved.

When the ratio of the N content to the Si content is less than the lower limit, the strain of the crystal structure is not sufficiently suppressed, and there is concern that toughness and the like may be degraded. On the other hand, when the ratio is higher than the upper limit, a composition which is less likely to be sintered is formed, and thus there is concern that the sintering density of the blank material 1 may be reduced and the mechanical properties may also be degraded.

The alloy contained in the blank material 1 may also contain C (carbon) in addition to the elements mentioned above. Due to the addition of C, the hardness and the tensile strength of the blank material 1 are further increased and the machinability is also further increased. Although the specific reasons that the machinability is further increased are not clear, a reduction in cutting resistance achieved by the generation of carbides is thought to be one of the reasons. Furthermore, since C and metal elements such as Co generate interstitial solid solutions, it is thought that a reduction in toughness (an increase in brittleness) rarely occurs even when C is added. Therefore, machinability can be enhanced while maintaining a certain degree of toughness.

The C content in the alloy contained in the blank material 1 is not particularly limited, and is preferably equal to or less than 1.5 mass % and more preferably equal to or less than 0.7 mass %. When the C content is higher than the upper limit, the brittleness of the blank material 1 is increased, and there is concern that mechanical properties may be degraded.

In addition, although the lower limit of the addition amount is not particularly set, the lower limit thereof is preferably set to be about 0.05 mass % in order to sufficiently exhibit the above-described effects.

In addition, the C content is preferably equal to or higher than 0.02 times and equal to or less than 0.5 times of the Si content and more preferably equal to or higher than 0.05 times and equal to or less than 0.3 times thereof. It is thought that by setting the ratio of C to Si to be in the above range, silicon oxides and carbides synergistically act to enhance machinability while minimizing an adverse effect on the mechanical properties of the blank material 1. Therefore, the blank material 1 having particularly excellent machinability can be obtained.

Furthermore, the N content is preferably equal to or higher than 0.3 times and equal to or less than 10 times of the C content and more preferably equal to or higher than 2 times and equal to or less than 8 times thereof. By setting the ratio of N to C to be in the above range, the enhancement of the machinability of the blank material 1 due to the addition of C and the enhancement of the mechanical properties of the blank material 1 due to the addition of N can be particularly allowed to coexist with each other.

Moreover, incorporation of a small amount of additives that are intentionally added in a range that does not impede the above-described effects and impurities that are unavoidably generated during the manufacture, into the alloy contained in the blank material 1 is also allowed in addition to the above-mentioned elements. In this case, the total content of the additives and the impurities is preferably equal to or less than 1 mass %, more preferably equal to or less than 0.5 mass %, and even more preferably equal to or less than 0.2 mass %. Examples of the elements of the additive and the elements of the impurities include Li, B, N, O, Na, Mg, Al, P, S, Mn, K, Ca, Sc, Ti, V, Co, Zn, Ga, Ge, Y, Pd, Ag, In, Sn, Sb, Hf, Ta, W, Os, Ir, Pt, Au, and Bi.

On the other hand, it is preferable that the alloy contained in the blank material 1 do not substantially contain Ni (nickel). In many cases, a certain amount of Ni is contained in an existing blank material in order to secure plastic workability. However, Ni is also an element that is treated as a causative agent of metal allergies and causes concern regarding the effect on a living body. In the alloy contained in the blank material 1, Ni as a constituent element is not added but Ni that is unavoidably incorporated during the manufacture may exist. Therefore, the metal frame machined from the blank material 1 is less likely to cause metal allergies and has particularly high compatibility with a living body. Since a desired amount of Si is added, a blank material 1 having sufficient machinability is realized even when Ni is not added thereto. In consideration of a case of unavoidable incorporation, the Ni content is preferably equal to or less than 0.05 mass % and more preferably equal to or less than 0.03 mass %.

In addition, in the alloy contained in the blank material 1, the remainder of the elements mentioned above is Co. As described above, the Co content is set to be highest among the elements contained in the alloy contained in the blank material 1.

In addition, the constituent elements of the alloy contained in the blank material 1 and the composition ratios thereof may be identified by, for example, the Iron and steel-Atomic absorption spectrometric method specified in JIS G 1257 (2000), the Iron and steel-ICP atomic emission spectrometric method specified in JIS G 1258 (2007), the Iron and steel-Method for spark discharge atomic emission spectrometric analysis specified in JIS G 1253 (2002), the Iron and steel-Method for X-ray fluorescence spectrometric analysis specified in JIS G 1256 (1997), and the gravimetry, titrimetry, and absorption photometry specified in JIS G 1211 to G 1237. Specifically, a solid atomic emission spectrometer (spark discharge emission spectrometer) manufactured by SPECTRO Analytical Instruments GmbH (model: Spectrolab, type: LAVMB08A) may be used.

In addition, JIS G 1211 to G 1237 are as follows.

JIS G 1211 (2011) Iron and steel-Methods for determination of carbon content

JIS G 1212 (1997) Iron and steel-Methods for determination of silicon content

JIS G 1213 (2001) Methods for determination of manganese content in iron and steel JIS G 1214 (1998) Iron and steel-Methods for determination of phosphorus content JIS G 1215 (2010) Iron and steel-Determination of sulfur content JIS G 1216 (1997) Iron and steel-Methods for determination of nickel content JIS G 1217 (2005) Iron and steel-Methods for determination of chromium content JIS G 1218 (1999) Iron and steel-Methods for determination of molybdenum content JIS G 1219 (1997) Iron and steel-Methods for determination of copper content JIS G 1220 (1994) Iron and steel-Methods for determination of tungsten content JIS G 1221 (1998) Iron and steel-Methods for determination of vanadium content JIS G 1222 (1999) Iron and steel-Methods for determination of cobalt content JIS G 1223 (1997) Iron and steel-Methods for determination of titanium content JIS G 1224 (2001) Methods for determination of aluminum content in iron and steel JIS G 1225 (2006) Iron and steel-Methods for determination of arsenic content JIS G 1226 (1994) Iron and steel-Method for determination of tin content JIS G 1227 (1999) Methods for determination of boron content in iron and steel JIS G 1228 (2006) Iron and steel-Methods for determination of nitrogen content JIS G 1229 (1994) Steel-Methods for determination of lead content JIS G 1232 (1980) Methods for determination of zirconium in steel JIS G 1233 (1994) Steel-Method for determination of selenium content JIS G 1234 (1981) Methods for determination of tellurium in steel JIS G 1235 (1981) Methods for determination of antimony in iron and steel JIS G 1236 (1992) Method for determination of tantalum in steel JIS G 1237 (1997) Iron and steel-Methods for determination of niobium content In addition, when C (carbon) and S (sulfur) are identified, particularly, oxygen flow combustion (high-frequency induction heating furnace combustion)-infrared absorption method specified in JIS G 1211 (2011) may also be used. Specifically, a carbon sulfur analyzer CS-200 manufactured by LECO Japan Corporation is used.

Furthermore, when N (nitrogen) and O (oxygen) are identified, particularly, Iron and steel-Methods for determination of nitrogen content specified in JIS G 1228 (2006) or General rules for determination of oxygen in metallic materials specified in JIS Z 2613 (2006) may also be used. Specifically, an oxygen nitrogen analyzer TC-300/EF-300 manufactured by LECO Japan Corporation is used.

In addition, the blank material 1 illustrated in FIG. 1 is formed of the sintered body of the metal powder that is manufactured by a powder metallurgy method. The blank material 1 has excellent mechanical properties such as hardness, tensile strength, proof stress, and elongation compared to, for example, a material manufactured by a casting method (ingot material). It is thought that this is based on features unique to a sintered body in which the blank material 1 manufactured by the powder metallurgy method is manufactured by using the metal powder obtained by quenching (has a small volume and is easily quenched), significant grain growth of metal crystals is less likely to occur compared to the casting method and the like, and thus enlarged metal crystals are less likely to be generated. In addition, according to the powder metallurgy method, the composition easily becomes homogeneous, and thus the distribution of Si or silicon oxides may be easily uniformized. Therefore, a blank material 1 having uniform machinability is obtained.

As the metal powder used to manufacture the blank material 1 (the metal powder for powder metallurgy according to the invention), a powder made of the above-described alloy is used. The average particle size of the powder is preferably equal to or greater than 3 µm and equal to or less than 100 µm, more preferably equal to or greater than 4 µm and equal to or less than 80 µm, and even more preferably equal to or greater than 5 µm and equal to or less than 60 µm. By using the metal powder having such particle sizes, a blank material 1 having high mechanical properties at a high density and excellent machinability can be manufactured.

The average particle size thereof is obtained by a particle size achieved when the cumulative amount of the metal powder on the small diameter side in terms of mass in a particle size distribution obtained by laser diffractometry becomes 50%.

In a case where the average particle size of the metal powder is less than the lower limit, the moldability in the powder metallurgy is degraded, and thus the density of the blank material 1 is degraded. Therefore, there is concern that the mechanical properties of the metal frame may be degraded. On the other hand, when the average particle size of the metal powder is higher than the upper limit, the filling property of the metal powder in the powder metallurgy is reduced, and thus the density of the blank material 1 is also reduced. Therefore, there is concern that the mechanical properties of the metal frame may be degraded. In addition, there is concern that the uniformity of the composition may be damaged and thus the machinability of the blank material 1 may be degraded.

It is preferable that the particle size distribution of the metal powder be as narrow as possible. Specifically, when the average particle size of the metal powder is in the above range, the maximum particle size thereof is preferably equal to or less than 200 µm, and more preferably equal to or less than 150 µm. By controlling the maximum particle size of the metal powder to be in the above range, the particle size distribution of the metal powder may be further narrowed. Therefore, further improvement in the mechanical properties and machinability of the blank material 1 can be achieved.

In addition, the maximum particle size thereof is a particle size achieved when the cumulative amount of the metal powder on the small diameter side in terms of mass in a particle size distribution obtained by laser diffractometry becomes 99.90.

When the short diameter of the particle of the metal powder is referred to as PS (µm) and the long diameter thereof is referred to as PL (µm), the average value of the aspect ratio defined as PS/PL is preferably about equal to or higher than 0.4 and equal to or less than 1, and more preferably about equal to or higher than 0.7 and equal to or less than 1. The shape of the metal powder having the aspect ratio is relatively close to a spherical shape, and thus the filling ratio thereof can be increased during compacting. As a result, a blank material 1 having high mechanical properties and machinability can be obtained.

The long diameter is the maximum length obtained in a projected image of a particle, and the short diameter is the maximum length in a direction orthogonal to the maximum length thereof. The average value of the aspect ratio is obtained by an average value of measurement values of 100 or more particles of the metal powder.

In a cross-section of the blank material 1, when the long diameter of the crystal structure is referred to as CL and the short diameter thereof is referred to as CS, the average value of the aspect ratio defined as CS/CL is preferably about equal to or higher than 0.4 and equal to or less than 1, and more preferably about equal to or higher than 0.5 and equal to or less than 1. The crystal structure having the aspect ratio has a low degree of anisotropy and thus contributes to the realization of the blank material 1 from which a metal frame having mechanical properties such as excellent proof stress regardless of the direction of an applied force can be manufactured. That is, the metal frame machined from the blank material 1 has excellent fracture resistance even when being used in any posture, and thus areas of use within the mouth are not limited, resulting in good usability. In other words, according to the blank material 1, a metal frame having excellent mechanical properties can be manufactured regardless of a method of machining the metal frame.

The long diameter is the maximum length that can be obtained by a single crystal structure from an observation image of the cross-section of the blank material 1, and the short diameter is the maximum length in a direction orthogonal to the maximum length thereof. In addition, the average value of the aspect ratio is obtained by an average value of measurement values of 100 or more crystal structures.

It is preferable that the blank material 1 include fine independent pores therein. Since the pores are included therein, the blank material 1 has particularly excellent machinability. It is thought that this is because since the independent pores are present, cut waste generated during cutting work are particularly easily separated from the body of the blank material 1 at the pores as starting points while suppressing the degradation in the mechanical properties of the blank material 1, thereby obtaining an action of significantly reducing cutting resistance.

Furthermore, since the blank material 1 has the pores, the metal frame machined from the blank material 1 also has pores which are open to the surface. The pores enable the constituent material of the porcelain to be incorporated when the porcelain is fused to the metal frame. This contributes to the enhancement in the adhesion between the metal frame and the porcelain. As a result, when a porcelain layer is provided to cover the surface of the metal frame, the exfoliation of the porcelain layer is suppressed, thereby obtaining a dental prosthesis having high reliability.

The average diameter of the pores is preferably equal to or greater than 0.1 μm and equal to or less than 10 μm, and more preferably equal to or greater than 0.3 μm and equal to or less than 8 μm. When the average diameter of the pores is in the above range, a blank material 1 having high machinability is obtained. That is, when the average diameter of the pores is less than the lower limit, there is concern that machinability may not be sufficiently increased. On the other hand, when the average diameter of the pores is higher than the upper limit, there is concern that the mechanical properties of the blank material 1 may be degraded.

In addition, the average diameter of the pores may be obtained by an average value of diameters of circles having the same areas as those of the pores in a scanning electron microscope image (projected area equivalent circle diameter). In addition, the average diameter of the pores is obtained by an average value of measurement values of 100 or more pores.

The area ratio of the pores to the observation image of the blank material 1 is preferably equal to or higher than 0.001% and equal to or less than 1%, and more preferably equal to or higher than 0.005% and equal to or less than 0.5%. When the area ratio of the pores is in the above range, the mechanical properties and the machinability of the blank material 1 can be allowed to coexist with each other at a higher degree.

The area ratio mentioned above is calculated by the ratio of an area occupied by the pores to the area of the observation image, and one side of the observation image is set to be about equal to or greater than 50 μm and equal to or less than 1000 μm.

Figure 4A:
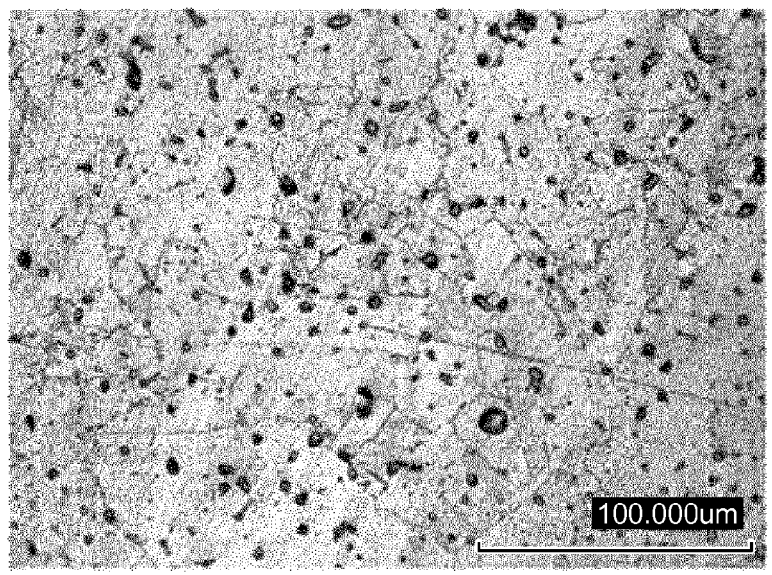
FIG. 4A is an example of an observation image of the blank material to be cut for dentistry according to the invention.
Figure 4B:
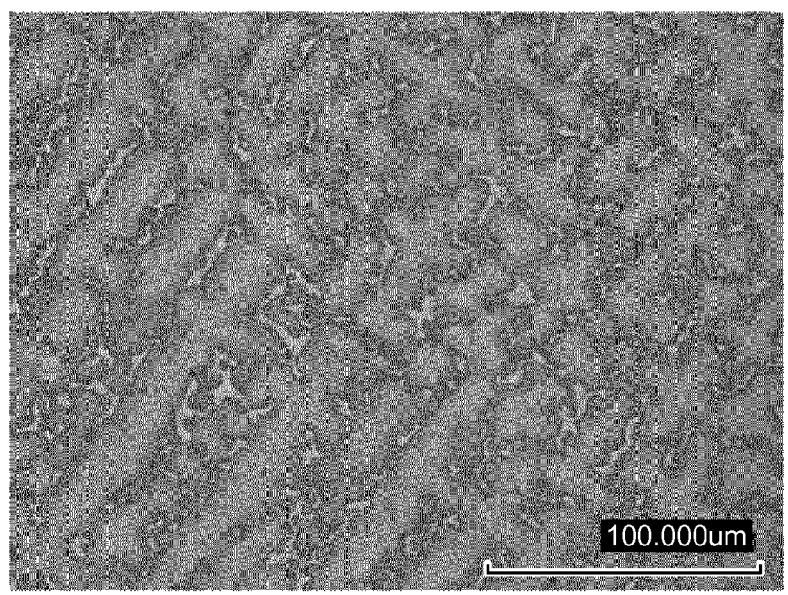
FIG. 4B is an example of an observation image of a blank material to be cut for dentistry according to the related art.

FIG. 4A is an example of the observation image of the blank material to be cut for dentistry according to the invention, and FIG. 4B is an example of an observation image of a blank material to be cut for dentistry according to the related art.

In the observation image illustrated in FIG. 4A, the presence of pores that are substantially uniformly dispersed is recognized. On the other hand, in the observation image illustrated in FIG. 4B, a dendritic structure (dendritic phase) is recognized.

The Vickers hardness of the blank material 1 is preferably equal to or higher than 200 and equal to or less than 480, and more preferably equal to or higher than 240 and equal to or less than 380. The blank material 1 having the hardness can be used to manufacture a metal frame having sufficient deformation resistance even against masticatory force. In addition, the blank material 1 having the hardness has relatively low cutting resistance, has excellent machinability, and thus can be efficiently machined into a metal frame having a desired shape and dimensions.

In addition, the Vickers hardness of the blank material 1 is measured on the basis of a test method specified in JIS Z 2244 (2009).

The tensile strength of the blank material 1 is preferably equal to or higher than 520 MPa, and more preferably equal to or higher than 600 MPa and equal to or less than 1500 MPa. The blank material 1 having the tensile strength can be used to manufacture a metal frame having excellent durability. In addition, machinability is also enhanced.

Similarly, the 0.2% proof stress of the blank material 1 is preferably equal to or higher than 450 MPa, and more preferably equal to or higher than 500 MPa and equal to or less than 1200 MPa. The blank material 1 having the 0.2% proof stress can be used to manufacture a metal frame having excellent durability. In addition, machinability is also enhanced.

The tensile strength and the 0.2% proof stress of the blank material 1 are measured on the basis of a test method specified in JIS Z 2241 (2011).

Furthermore, the elongation of the blank material 1 is preferably equal to or higher than 2% and equal to or less than 50%, and more preferably equal to or higher than 10% and equal to or less than 45%. The blank material 1 having the elongation is less likely to have defects or cracks and thus has excellent machinability.

The elongation (elongation at break) of the blank material 1 is measured on the basis of a test method specified in JIS Z 2241 (2011).

The Young's modulus of the blank material 1 is preferably equal to or higher than 150 GPa, and more preferably equal to or higher than 170 GPa and equal to or less than 300 GPa. The blank material 1 having the above Young's modulus is less likely to be deformed, and thus enables cutting work at high dimensional accuracy, thereby realizing a metal frame which is less likely to be deformed by masticatory force. In addition, machinability is also enhanced.

Furthermore, the fatigue strength of the blank material 1 is preferably equal to or higher than 250 MPa, more preferably equal to or higher than 350 MPa, and even more preferably equal to or higher than 500 MPa and equal to or less than 1000 MPa. The generation of fatigue cracks in the blank material 1 having the fatigue strength is suppressed even when the blank material 1 is used in an environment on which repeated load is applied, for example, while coming into contact with a body fluid in the mouth, thereby realizing a metal frame capable of exhibiting the functions over a long period of time.

In addition, the fatigue strength of the blank material 1 is measured on the basis of a test method specified in JIS T 0309 (2009). An application waveform of a load corresponding to repeated stress is referred to as a sinusoidal waveform, and a stress ratio (minimum stress/maximum stress) is set to 0.1. In addition, repetition frequency is set to 30 Hz, and the number of times of repetition is set to $1 \times 10^7$.

The blank material 1 has low cutting resistance as described above and thus has excellent machinability.

That is, the cutting resistance of the blank material 1 is lower than the cutting resistance of an ingot material having the same composition as the metal powder used to manufacture the blank material 1. Reducing cutting resistance is connected to suppressing the amplitude of vibration in a working tool during cutting to be low. Therefore, when cutting work is performed on the blank material 1, the blank material 1 can be easily and accurately machined into a desired shape, thereby manufacturing a metal frame having high dimensional accuracy.

Specifically, the cutting resistance of the blank material 1 is preferably equal to or less than 300 N, more preferably equal to or less than 250 N, and even more preferably equal to or less than 200 N. The blank material 1 which can be worked with relatively low cutting resistance has high machinability and can be worked at high working accuracy.

In addition, the cutting resistance of the blank material 1 may be measured by using, for example, a three-component tool dynamometer.

Figure 5:
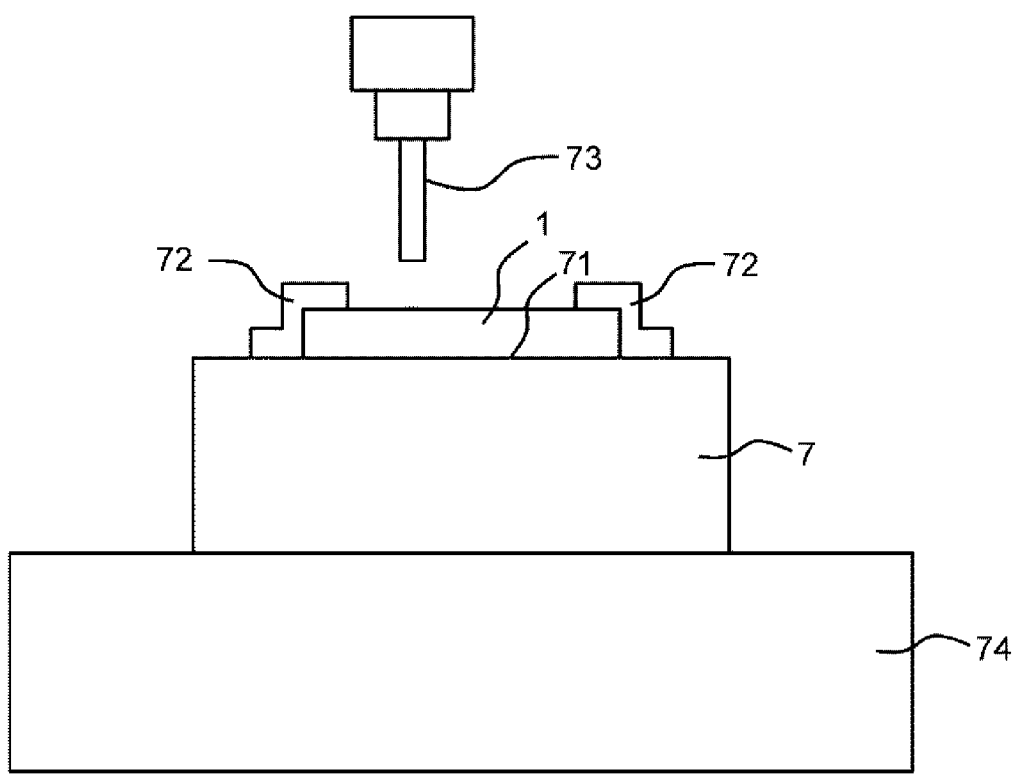
FIG. 5 is a view illustrating a method of measuring the cutting resistance of the blank material to be cut for dentistry according to the invention.

FIG. 5 is a view illustrating a method of measuring the cutting resistance of the blank material 1.

In order to measure the cutting resistance of the blank material 1, first, as illustrated in FIG. 5, a three-component tool dynamometer 7 is placed on a stage 74 of a working apparatus. Next, the blank material 1 is fixed onto a measuring unit 71 of the three-component tool dynamometer 7. A fixing tool 72 which uses screws is used for the fixing, and a fastening torque of the screws is set to 30 kN. The blank material 1 is subjected to cutting work by using the working tool 73 in this state. In addition, among the cutting resistances of components in three directions (x component, y component, and z component) measured during the work by the three-component tool dynamometer 7, the maximum value thereof may be employed as the cutting resistance of the blank material 1. In addition, cutting resistance in wet work is the cutting resistance when work is performed by using a cutting liquid.

Figure 6A:
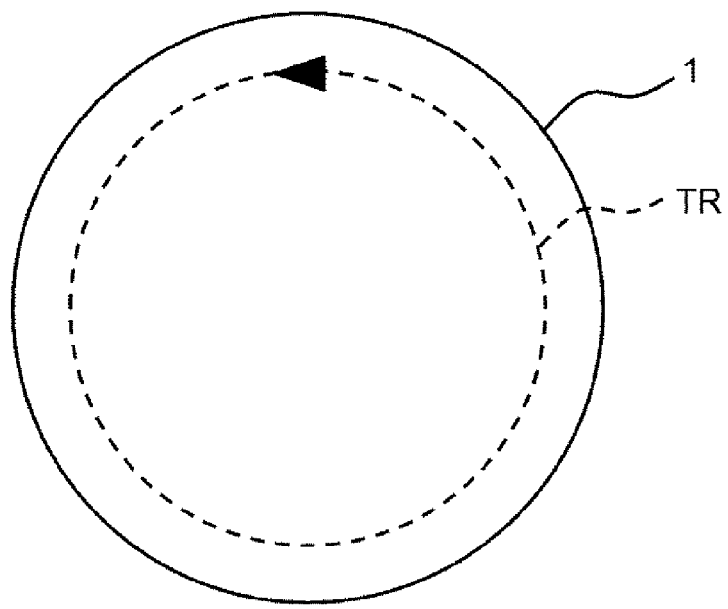
FIGS. 6A and 6B are views illustrating traces on which the blank material is scanned by a working tool when the cutting resistance of the blank material to be cut for dentistry according to the invention is measured.
Figure 6B:
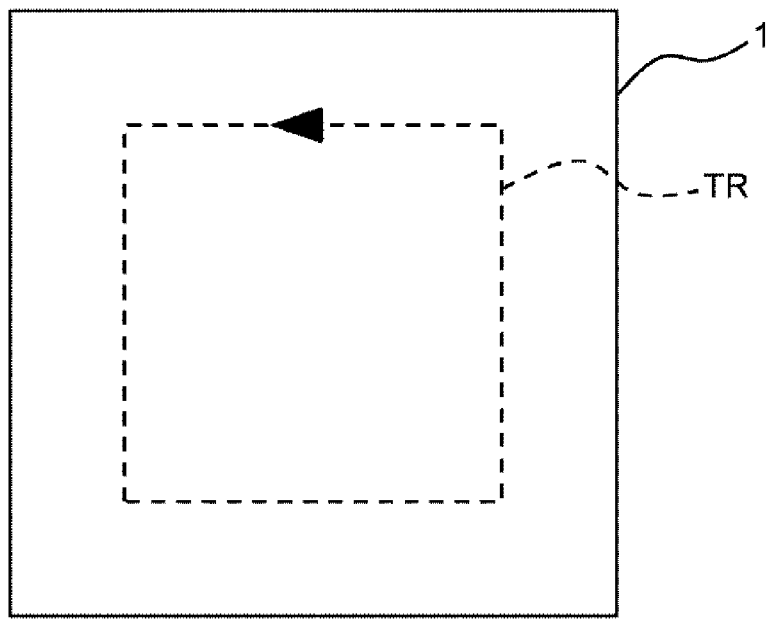

FIGS. 6A and 6B are views illustrating traces TR on which the blank material 1 is scanned by the working tool 73 when the cutting resistance of the blank material 1 is measured. In a case of measuring the cutting resistance of the blank material 1, the working tool 73 may perform scanning on the trace TR along the external shape of the blank material 1. For example, when the external shape of the blank material 1 is a circular shape, as illustrated in FIG. 6A, the working tool 73 may perform scanning on the trace TR to draw the circular shape, and when the external shape of the blank material 1 is a square shape, as illustrated in FIG. 6B, the working tool 73 may scan the trace TR to draw the square shape.

In addition, as the metal powder used to manufacture the blank material 1, for example, a metal powder produced by various powdering methods such as atomization (for example, water atomization, gas atomization, and spinning water atomization), reduction process, carbonyl process, and pulverization may be used.

Among these, a metal powder produced by atomization is preferably used, and a metal powder produced by water atomization or spinning water atomization is more preferably used. The atomization is a method of allowing molten metal to collide with a fluid (liquid or gas) ejected at a high speed to atomize and cool the molten metal, thereby producing a metal powder. By producing the metal powder according to the atomization, very fine powder can be efficiently produced. In addition, the particle shape of the obtained powder is close to a spherical shape due to the action of surface tension. Therefore, a compact having a high filling rate is obtained when the metal powder is molded by the powder metallurgy method. As a result, a blank material 1 having excellent mechanical properties is obtained.

In a case where water atomization is used as the atomization, the pressure of water ejected toward the molten metal (hereinafter, referred to as "atomized water") is not particularly limited, and is preferably about equal to or higher than 75 MPa and equal to or less than 120 MPa (equal to or higher than 750 kgf/cm$^2$ and equal to or less than 1200 kgf/cm$^2$) and more preferably about equal to or higher than 90 MPa and equal to or less than 120 MPa (equal to or higher than 900 kgf/cm$^2$ and equal to or less than 1200 kgf/cm$^2$).

The temperature of the atomized water is not particularly limited, and is preferably equal to or higher than 1° C. and equal to or less than 20° C.

Furthermore, in many cases, the atomized water has the vertex on the dropping path of the molten metal, and is ejected into a conical shape in which the outside diameter gradually reduces downward. In this case, the vertex angle θ of the cone formed by the atomized water is preferably equal to or greater than 10° and equal to or less than 40°, and more preferably equal to or greater than 15° and equal to or less than 35°. Accordingly, a metal powder having the above-described composition can be reliably produced.

According to the water atomization (particularly the spinning water atomization process), the molten metal can be particularly rapidly cooled. Therefore, a uniform blank material 1 having excellent mechanical properties and machinability is obtained.

The cooling rate when the molten metal is cooled in the atomization is preferably equal to or higher than $1 \times 10^{4°}$ C./s, and more preferably equal to or higher than $1 \times 10^{5°}$ C./s. Due to the rapid cooling, a metal powder having a particularly small metal crystal grain size is obtained.

In addition, in order to obtain the molten metal by melting a raw material, when the melting point of the constituent material of the blank material 1 is referred to as Tm, the melting temperature of the raw material is preferably set to be about equal to or higher than Tm+50° C. and equal to or less than Tm+300° C., and more preferably set to be about equal to or higher than Tm+100° C. and equal to or less than Tm+200° C. Accordingly, when the molten metal is allowed to collide with the fluid to be atomized, the production of the alloy can be controlled to be constant. That is, an alloy having a high purity (low oxygen content) is easily produced while suppressing the enlargement of the crystal structure.

Therefore, a metal powder which is particularly appropriate for the manufacturing of the blank material 1 can be produced.

The metal powder obtained as above is molded by various molding methods to obtain a compact. Examples of the molding methods include press molding, extrusion molding, and injection molding.

Thereafter, the obtained compact is degreased and baked, thereby obtaining a sintered body (the blank material 1). The baking temperature is set depending on the alloy composition, and as an example, is set to be equal to or higher than 900° C. and equal to or less than 1400° C.

In addition, a HIP treatment (hot isostatic pressing treatment) or the like may further be performed on the sintered body obtained as above. Accordingly, further densification of the sintered body is achieved, thereby obtaining a blank material 1 having better mechanical properties.

The conditions of the HIP treatment include, for example, a temperature of equal to or higher than 850° C. and equal to or less than 1200° C. and a time of about equal to or longer than 1 hour and equal to or shorter than 10 hours.

The pressurization pressure is preferably equal to or higher than 50 MPa and more preferably equal to or higher than 100 MPa.

The blank material 1 is formed of the sintered body obtained by solutionizing N in the metal material during and after the powder production and using the obtained powder. Therefore, in the blank material 1, N is substantially uniformly distributed and the physical properties thereof can be allowed to be substantially uniform. Therefore, when plural metal frames are machined from the blank material 1, the properties of the metal frames can be uniformized, thereby suppressing individual differences.

Specifically, for example, when the thickness of the blank material 1 is equal to or greater than 10 mm, in the cross-section of the blank material 1 in the thickness direction, a position at a depth of 0.3 mm from the surface is referred to as a surface layer portion and a position at a depth of 5 mm from the surface is referred to as an inner layer portion.

At this time, the concentration of N in the inner layer portion is preferably equal to or higher than 50% and equal to or less than 200% of the concentration of N in the surface layer portion, more preferably equal to or higher than 60% and equal to or less than 175%, and even more preferably equal to or higher than 75% and equal to or less than 150%. When the concentration of N in the inner layer portion is less than the lower limit or higher the upper limit, the physical properties of the inner layer portion and the surface layer portion are different from each other. Therefore, there is concern that machinability may change during the cutting when the cutting work is performed on the blank material 1. As such, there is concern that the dimensional accuracy of the machined metal frame may be degraded. In addition, there is concern that the mechanical properties of the metal frame may partially vary.

In addition, the concentrations of N in the inner layer portion and the surface layer portion may be obtained on the basis of quantitative analysis of N by the electron probe microanalyzer (EPMA). At this time, by performing line analysis from the surface to the inside of the blank material 1, the distribution of the concentration of N in the thickness direction of the blank material 1 is obtained. Accordingly, the concentration of N in the inner layer portion and the exterior portion described above can be efficiently obtained.

In the blank material 1, the Vickers hardness of the inner layer portion is preferably equal to or higher than 67% and equal to or less than 150% of the Vickers hardness of the surface layer portion and more preferably equal to or higher than 75% and equal to or less than 125%. When the concentration of N in the inner layer portion is less than the lower limit or higher than the upper limit, the hardness of the inner layer portion and the hardness of the surface layer portion are different from each other. Therefore, there is concern that cutting properties may also change during the cutting when the cutting work is performed on the blank material 1. Therefore, there is concern that the dimensional accuracy of the machined metal frame may be degraded.

In addition, in the blank material 1, the difference in various physical properties (for example, the difference in cutting resistance which will be described later) between the inner layer portion and the surface layer portion is small.

It is thought that the homogeneity of the blank material 1 is caused by, in addition to that the blank material 1 is formed of the sintered body produced by powder metallurgy, that the blank material 1 is formed of the sintered body produced by solutionizing N in the metal material during and after the power production and performing the powder metallurgy method using the power. In order to cause N to be solutionized in the metal material during the powder production, for example, a method of nitrifying at least one type of Co, Cr, Mo, and Si contained in the raw material in advance, a method of maintaining the molten metal in a nitrogen gas atmosphere during or after the melting of the raw material, a method of injecting (bubbling) nitrogen gas into the molten metal, or the like is used.

In addition, there is also a method of allowing the alloy to be impregnated with N by heating the compact obtained by molding the metal powder or the sintered body obtained by sintering the compact in a nitrogen gas atmosphere or performing the HIP treatment in a nitrogen gas atmosphere (nitrification treatment). However, in this method, the compact or the sintered body is less likely to be uniformly nitrified from the surface layer portion to the inner layer portion, and even if the uniform nitrification is achieved, the nitrification is desirably performed by taking a very long time while suppressing the nitrification rate. Therefore, there is a problem from the viewpoint of manufacturing efficiency of the blank material.

In a case where the compact obtained by solutionizing N in the powder is degreased and baked, the compact is degreased and baked in an inert gas such as nitrogen gas or argon gas, thereby suppressing a change in the concentration of N being solutionized.

In addition, it is thought that the homogeneity of the blank material 1 is associated with the ratio (N/Si) of the N content to the Si content. That is, it is thought that when the N/Si is in the above range, the strain of the crystal structure caused by the solutionizing of Si is suppressed by the solutionizing of N, resulting in an increase in the homogeneity of the blank material 1.

As described above, the blank material 1 is characterized by a small difference in cutting resistance between the surface layer portion and the inner layer portion. Therefore, a change in the cutting resistance while the cutting work is performed on the blank material 1 is suppressed, and thus the degradation in the dimensional accuracy of the machined metal frame can be suppressed.

Specifically, for example, when the blank material 1 has a plate shape and the thickness of the blank material is equal to or greater than 10 mm, in the cross-section of the blank material 1 in the thickness direction, a position at a depth of 0.3 mm from the surface is referred to as a surface layer portion and a position at a depth of 5 mm from the surface is referred to as an inner layer portion.

At this time, the cutting resistance in the inner layer portion is preferably equal to or higher than 50% and equal to or less than 200% of the cutting resistance in the surface layer portion, more preferably equal to or higher than 60% and equal to or less than 175%, and even more preferably equal to or higher than 75% and equal to or less than 150%. Accordingly, the degradation in the working accuracy of the blank material 1 caused by variations in the cutting resistance can be suppressed. When the cutting resistance in the inner layer portion is less than the lower limit, the difference between the cutting resistance in the inner layer portion and the cutting resistance in the surface layer portion increases. Therefore, there is concern that the working accuracy may be degraded depending on the positional relationship between the blank material 1 and the working tool. That is, since the cutting resistance in the inner layer portion is much lower than the cutting resistance in the surface layer portion, for example, when the working tool that performs work on the surface layer portion gradually moves to the inner layer portion, the cutting resistance decreases. Therefore, there is concern that the relationship between the driving force and the cutting result may be collapsed and unintended work may be performed. On the other hand, even in a case where the cutting resistance in the inner layer portion is higher than the upper limit, similarly, there is concern that the working accuracy may be degraded depending on the positional relationship between the blank material 1 and the working tool. That is, since the cutting resistance in the inner layer portion is much higher than the cutting resistance in the surface layer portion, for example, when the working tool that performs work on the surface layer portion gradually moves to the inner layer portion, the cutting resistance increases. Therefore, there is concern that the relationship between the driving force and the cutting result may be collapsed and unintended work may be performed.

In addition, the blank material 1 is useful in not only wet cutting work but also dry cutting work since the cutting resistance of the blank material 1 is relatively suppressed. That is, the blank material 1 is characterized by a small difference between the cutting resistance in the wet cutting work and the cutting resistance in the dry cutting work. Therefore, depending on the shape of the metal frame machined from the blank material 1, the metal frame having high dimensional accuracy can be machined even by the dry cutting work.

Specifically, when the cutting resistance in the wet cutting work is assumed to be 1, the cutting resistance in the dry cutting work is preferably equal to or less than 2, and more preferably equal to or less than 1.5. When the cutting resistance in the dry cutting work is in the above range with respect to the cutting resistance in the wet cutting work, a metal frame having sufficiently high dimensional accuracy can be machined even by the dry cutting work. Therefore, the blank material 1 is useful in terms of enabling easy cutting work.

According to the dry cutting work, the cutting liquid does not need to be used, and thus there is an advantage in that an effort to wash the machined metal frame can be reduced. Particularly in a case of being retained in the body like the metal frame, cutting liquid residues should be avoided as much as possible. Therefore, employing the dry cutting work is effective in terms of the safety of the machined metal frame and the like.

In addition, in the wet cutting work performed on the blank material 1, even in a case of using an aqueous cutting liquid instead of an oil-based cutting liquid, good cutting results are obtained. The aqueous cutting liquid can be relatively easily removed and thus the effort to wash the liquid can be suppressed. Furthermore, the blank material 1 can obtain good cutting results even in semi-dry work (MQL work) in which work is performed using a small amount of cutting liquid. Therefore, a metal frame having high dimensional accuracy can be machined while significantly suppressing the amount of cutting liquid being used.

Metal Frame for Porcelain Fusing for Dentistry

Next, an embodiment of the metal frame for porcelain fusing for dentistry according to the invention will be described.

Figure 7:
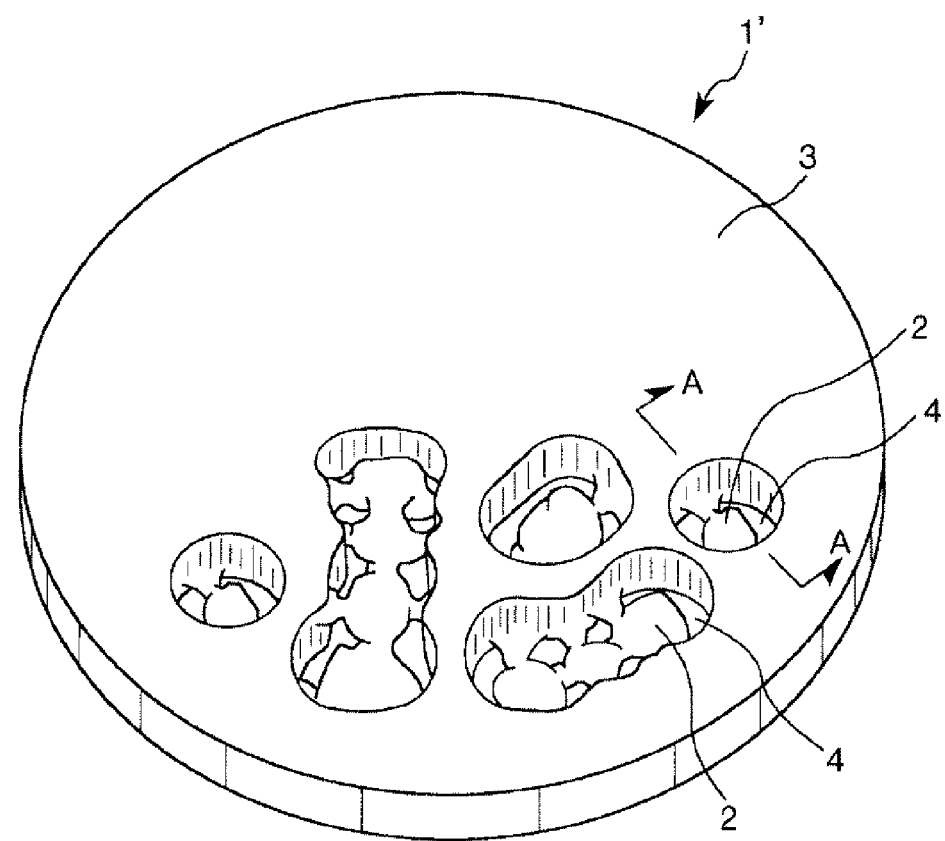
FIG. 7 is a perspective view illustrating a state after machining an embodiment of the invention of a metal frame for porcelain fusing for dentistry from the blank material illustrated in FIG. 1.
Figure 8:
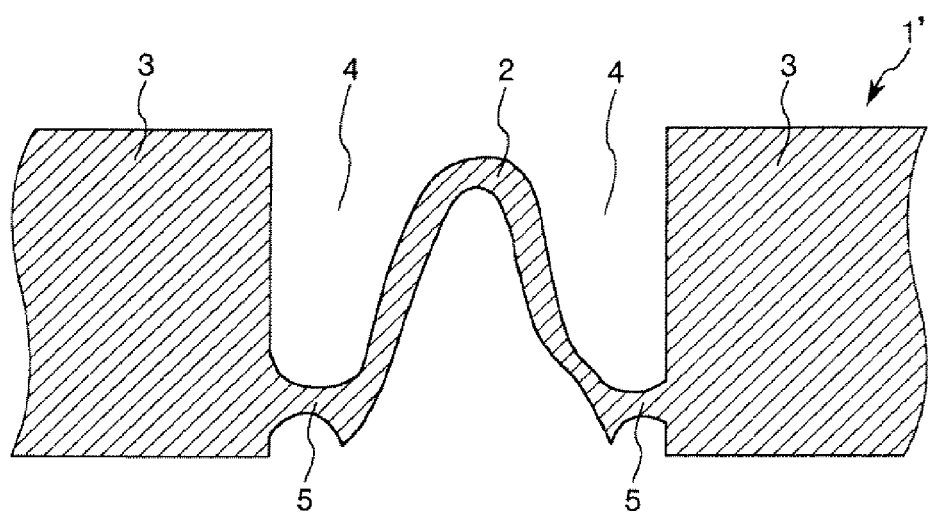
FIG. 8 is a cross-sectional view taken along line A-A of FIG. 7.
Figure 9:
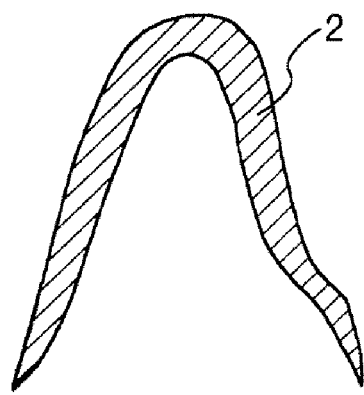
FIG. 9 is a longitudinal cross-sectional view illustrating the embodiment of the invention of the metal frame for porcelain fusing for dentistry.

FIG. 7 is a perspective view illustrating a state after machining the embodiment of the metal frame for porcelain fusing for dentistry according to the invention from the blank material illustrated in FIG. 1, FIG. 8 is a cross-sectional view taken along line A-A of FIG. 7, and FIG. 9 is a longitudinal cross-sectional view illustrating the embodiment of the metal frame for porcelain fusing for dentistry according to the invention.

A blank material 1' after being cut as illustrated in FIG. 7 is in a state where a metal frame 2 is machined by performing the cutting work on the blank material 1. The metal frame 2 is a member used as a base material of a dental prosthesis such as inlays, crowns, bridges, metal bases, artificial teeth, implants, abutments, fixtures, and screws. Therefore, a rough shape of the dental prosthesis is determined by the metal frame 2, and thus the shape of the machined metal frame 2 generally corresponds to a shape of the dental prosthesis to be manufactured. In addition, by providing a porcelain layer on the surface of the metal frame 2, the dental prosthesis which will be described later is obtained.

In addition, although the metal frame for porcelain fusing is particularly described herein, the metal frame according to the invention may not be provided for porcelain fusing, for example, may be dental metal components such as inlays, crowns, bridges, metal bases, artificial teeth, implants, abutments, fixtures, and screws.

In the cutting work, any cutting machine may be used. For example, a machining center, a milling machine, a drilling machine, or a lathe may be employed. Among these, a cutting machine embedded in a CAM system is preferably used. According to the cutting machine, a model acquired by the CAD system or the like can be sufficiently reflected to working results, thereby contributing to the realization of a dental prosthesis having low wearing incompatibility particularly for a patient.

The blank material 1' after being cut as illustrated in FIGS. 7 and 8 includes a flat plate portion 3 derived from the blank material 1, and the metal frame 2 machined to be surrounded by a through-hole 4 formed in the flat plate portion 3. As illustrated in FIG. 8, the metal frame 2 and the flat plate portion 3 are connected by small connection portions 5, and finally by cutting the connection portions 5, the metal frame 2 can be separated from the blank material 1' after being cut.

The metal frame 2 illustrated in FIG. 9 is illustrated in a state of being separated from the blank material 1' after being cut as illustrated in FIGS. 7 and 8. The shape of the metal frame 2 illustrated in FIG. 9 is an example, and the metal frame 2 has various shapes depending on the type of the dental prosthesis.

As desired, a polishing treatment may be performed on the obtained metal frame 2. Examples of the polishing treatment include barrel polishing and sandblasting.

Furthermore, as desired, secondary work may be performed on the obtained metal frame 2. Examples of the secondary work include machining work such as cutting and grinding, laser processing, electron beam processing, water-jet machining, electric discharge machining, press working, extruding, rolling, forging, bending, spinning, drawing, component rolling, and shearing.

The metal frame 2 obtained in this manner has high dimensional accuracy due to the excellent machinability of the blank material 1 as described above. Since the metal frame 2 can be mounted on an affected area with low incompatibility, a burden on the patient is minimized. In addition, when the porcelain layer is provided on the surface of the metal frame 2, high adhesion and high aesthetics of the porcelain layer can be realized.

The metal frame 2 has high corrosion resistance and thus has excellent compatibility with a living body.

Furthermore, the metal frame 2 has excellent mechanical properties and thus is less likely deformed by masticatory force and has excellent durability.

After separating the metal frame 2 from the blank material 1' after the cutting work, the remaining flat plate portion 3 may be used to cut another metal frame 2 or may also be recycled into a raw material for manufacturing a new blank material 1. That is, the remaining flat plate portion 3 is melted and powdered by atomization or the like, thereby obtaining the metal powder used to manufacture the blank material 1 (the metal powder for powder metallurgy according to the invention).

Dental Prosthesis

Next, an embodiment of the dental prosthesis according to the invention will be described.

Figure 10:
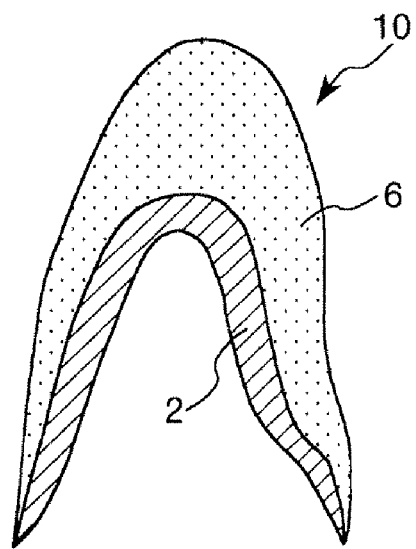
FIG. 10 is a longitudinal cross-sectional view illustrating an embodiment of a dental prosthesis according to the invention.

FIG. 10 is a longitudinal cross-sectional view illustrating the embodiment of the dental prosthesis according to the invention.

A dental prosthesis 10 illustrated in FIG. 10 includes the metal frame 2 and a porcelain layer 6 provided to cover a portion of the surface thereof.

The porcelain layer 6 is a part in charge of the aesthetics of the dental prosthesis 10 and generally has a color close to the tooth color of the patient.

Examples of the constituent material of the porcelain layer 6 include various types of ceramic-based materials including feldspar, quartz, porcelain clay, and metal oxides and various types of resin materials. Among these, from the viewpoint of aesthetics and the adhesion to the metal frame 2, the ceramic-based materials are preferably used. Specifically, alumina, silica, lithium oxide, sodium oxide, potassium oxide, calcium oxide, iron oxide, magnesia, zirconia, titania, antimony oxide, cerium oxide, and the like may be employed, and a mixture of one type or two or more types thereof is used.

A slurry containing the constituent material is applied to the surface of the metal frame 2 and is thereafter subjected to a fusing treatment, thereby forming the porcelain layer 6.

Among these, the constituent material of the porcelain layer 6 preferably contains alumina. When the ceramic material containing alumina is fused to the surface of the metal frame 2, a mullite phase is generated in the vicinity of the interface between the porcelain layer 6 and the metal frame 2. It is thought that the mullite phase is generated by mixing of the alumina contained in the ceramic material and Si or silicon oxide contained in the metal frame 2. Therefore, the porcelain layer 6 and the metal frame 2 come in close contact with each other via the mullite phase, so that the porcelain layer 6 is less likely to be exfoliated and a dental prosthesis having high reliability is obtained. In addition, it is thought that as the mullite phase is generated, wettability of the ceramic material for the metal frame 2 is enhanced during the fusing treatment. Therefore, from this point of view, the adhesion of the porcelain layer 6 is thought to be increased, and furthermore, the porcelain layer 6 can be evenly fused.

The alumina content of the constituent material of the porcelain layer 6 is preferably about equal to or higher than 2 mass % and equal to or less than 50 mass %, more preferably about equal to or higher than 4 mass % and equal to or less than 35 mass %, and even more preferably about equal to or higher than 6 mass % and equal to or less than 25 mass %. By setting the alumina content to be in the above range, alumina is necessarily and sufficiently secured to enhance the adhesion between the porcelain layer 6 and the metal frame 2, and the mechanical properties of the porcelain layer 6 itself are also enhanced. Accordingly, a dental prosthesis 10 having higher reliability is obtained.

Therefore, when the alumina content is less than the lower limit, a sufficient amount of mullite phase is not generated between the porcelain layer 6 and the metal frame 2, the wettability of the ceramic material is degraded, and thus there is concern that the adhesion of the porcelain layer 6 may be degraded. On the other hand, when the alumina content is higher than the upper limit, the degradation in mechanical properties such as brittleness of the porcelain layer 6 is likely to occur, and thus there is concern that the adhesion of the porcelain layer 6 may also be degraded.

The average thickness of the porcelain layer 6 is not particularly limited, and is preferably about equal to or greater than 0.05 mm and equal to or less than 3 mm and more preferably about equal to or greater than 0.2 mm and equal to or less than 2 mm. By setting the average thickness of the porcelain layer 6 to be in the above range, the adhesion of the porcelain layer 6 to the metal frame 2 can be further increased. In addition, desired and sufficient light shielding properties are imparted on the porcelain layer 6, and thus the color of the metal frame 2 is less likely to be seen through the porcelain layer 6, thereby obtaining a dental prosthesis 10 having excellent aesthetics.

When the porcelain layer 6 is formed, first, the constituent material of the porcelain layer 6 is finely ground by a ball mill, a planetary mill, or the like. Thereafter, as desired, a heat treatment is performed on the resultant in a range of equal to or higher than 800° C. and equal to or less than 1100° C. for about 30 minutes or longer and 60 minutes or shorter.

The ground material obtained in this manner is dispersed by a dispersion medium to be prepared into a slurry form or a paste form. Accordingly, a slurry or paste for forming the porcelain layer 6 is obtained. As the dispersion medium, there are water, propylene glycol, ethylene glycol, glycerin, polymethyl methacrylate, polyvinyl acetate, cellulose nitrate, ethyl cellulose, and the like.

The obtained slurry or paste is applied to the surface of the metal frame 2 and is subjected to the fusing treatment. The fusing temperature is set depending on the constituent material of the porcelain layer 6, and for example, is set to be equal to or higher than 500° C. and equal to or less than 1000° C. In this manner, the dental prosthesis 10 is obtained.

While the blank material to be cut for dentistry, the metal powder for powder metallurgy, the metal frame for porcelain fusing for dentistry, and the dental prosthesis according to the invention have been described on the basis of the preferred exemplary embodiments, the invention is not limited thereto.

For example, in the embodiments, a case where a plurality of metal frames for porcelain fusing for dentistry are machined from the blank material to be cut for dentistry has been described. However, the invention is not limited to this case and may also be applied to a case where a single metal frame is machined from a single blank material 1.

EXAMPLES

Next, specific examples exemplifying the principles of the invention will be described.

1. Manufacturing of Blank Material to be Cut for Dentistry

Sample No. 1

(1) First, a raw material was melted in a high-frequency induction furnace and was atomized by water atomization, thereby obtaining a metal powder. Next, the metal powder was classified by using a standard sieve having a mesh size of 150 μm. The alloy composition of the obtained metal powder is shown in Table 1. In addition, N is included in the raw material in a state of being bonded to Cr (chromium nitride state). In order to specify the alloy composition, a solid atomic emission spectrometer (spark emission spectrometer) manufactured by SPECTRO Analytical Instruments GmbH in a model of Spectrolab and a type of LAVMB08A was used. For the quantitative analysis of C (carbon), a carbon sulfur analyzer CS-200 manufactured by LECO Japan Corporation was used.

(2) Next, a binder solution was prepared by dissolving an organic binder in water. The amount of the organic binder in the binder solution was 10 g per 1 kg of the metal powder. In addition, the amount of water in the binder solution was 50 g per 1 g of the organic binder.

(3) Next, the metal powder was input to a treatment container of a granulating apparatus. In addition, the metal powder was granulated by a spray dry method while spraying the binder solution toward the metal powder in the treatment container from a spray nozzle of the granulating apparatus, thereby obtaining granulated powder.

(4) Next, the obtained granulated powder was molded under the following molding conditions, thereby obtaining a compact.

<Molding Conditions>
Molding method: compacting
Molding pressure: 300 MPa (3 t/cm$^2$)

(5) Next, the compact was degreased under the following decreasing conditions, thereby obtaining a degreased body.

<Degreasing Conditions>
Heating temperature: 470° C.
Heating time: 1 hour
Heating atmosphere: nitrogen atmosphere (6) Next, the obtained degreased body was baked under the following baking conditions, thereby obtaining a sintered body (blank material to be cut for dentistry). The obtained blank material to be cut for dentistry had a disk shape having a diameter of 100 mm and a thickness of 15 mm.

<Baking Conditions>
Heating temperature: 1300° C.
Heating time: 3 hours
Heating atmosphere: argon atmosphere Sample Nos. 2 to 16

Blank materials to be cut for dentistry were obtained in the same manner as the case of Sample No. 1 except that the manufacturing conditions were set to the conditions shown in Table 1.

Sample Nos. 17 to 20

When the raw material was melted in the high-frequency induction furnace, nitrogen gas was injected into the molten metal. At this time, by changing the injection time, the N content was changed.

In addition, blank materials to be cut for dentistry were obtained in the same manner as the case of Sample No. 1 except that the other manufacturing conditions were set as shown in Table 1.

Sample Nos. 21 to 24

First, by using a raw material that does not contain N, a metal powder was obtained in the same manner as the case of Sample No. 1.

Next, sintered bodies were obtained in the same manner as the case of Sample No. 1 except that this metal powder was used and the heating atmosphere of the baking conditions was changed to a mixed gas atmosphere of 50 volume % of argon and 50 volume % of nitrogen. At this time, by changing the partial pressure of the nitrogen gas, the N content in the metal powder was changed.

In addition, blank materials to be cut for dentistry were obtained in the same manner as the case of Sample No. 1 except that the other manufacturing conditions were set as shown in Table 1.

Sample Nos. 25 to 26

When the raw material was melted in the high-frequency induction furnace, nitrogen gas was injected into the molten metal. At this time, by changing the injection time, the N content in the metal powder was changed.

In addition, blank materials to be cut for dentistry were obtained in the same manner as the case of Sample No. 1 except that the other manufacturing conditions were set as shown in Table 1.

Sample Nos. 27 to 29

When the raw material was melted in the high-frequency induction furnace, after nitrogen gas was injected into the molten metal, the molten metal was poured into a mold having the shape of the blank material, thereby obtaining a casted body. At this time, by changing the injection time, the N content in the metal powder was changed.

In addition, blank materials to be cut for dentistry were obtained in the same manner as the case of Sample No. 1 except that the other manufacturing conditions were set as shown in Table 1.

The manufacturing conditions of the blank materials to be cut for dentistry of the above Samples Nos. are shown in Tables 1 and 2.

TABLE 1

| | | Blank material to be cut for dentistry Alloy composition | | | | | | |
|---|---|---|---|---|---|---|---|---|
| | | Cr | Mo | Si | C | N | Ni | Co |
| | | | | | mass % | | | |
| Sample No. 1 | Example | 29.8 | 6.80 | 0.78 | 0.02 | 0.13 | 0.01 | Remainder |
| Sample No. 2 | Example | 27.3 | 8.43 | 0.96 | 0.04 | 0.18 | 0.01 | Remainder |
| Sample No. 3 | Example | 28.5 | 7.21 | 0.83 | 0.03 | 0.12 | 0.01 | Remainder |

TABLE 1-continued

| | | Blank material to be cut for dentistry Alloy composition | | | | | | |
|---|---|---|---|---|---|---|---|---|
| | | Cr | Mo | Si | C | N | Ni | Co |
| | | | | | mass % | | | |
| Sample No. 4 | Example | 26.1 | 5.32 | 0.34 | 0.02 | 0.09 | 0.01 | Remainder |
| Sample No. 5 | Example | 31.9 | 6.50 | 0.71 | 0.07 | 0.23 | 0.01 | Remainder |
| Sample No. 6 | Example | 33.5 | 9.27 | 0.65 | 0.13 | 0.28 | 0.01 | Remainder |
| Sample No. 7 | Example | 34.9 | 11.80 | 0.95 | 0.35 | 0.27 | 0.01 | Remainder |
| Sample No. 8 | Example | 27.1 | 5.49 | 0.96 | 0.07 | 0.11 | 0.01 | Remainder |
| Sample No. 9 | Example | 26.1 | 5.11 | 0.83 | 0.04 | 0.12 | 0.02 | Remainder |
| Sample No. 10 | Example | 29.9 | 10.75 | 0.65 | 1.19 | 0.21 | 0.02 | Remainder |
| Sample No. 11 | Example | 29.8 | 6.80 | 0.78 | 0.05 | 0.26 | 0.01 | Remainder |
| Sample No. 12 | Example | 27.3 | 8.43 | 0.96 | 0.04 | 0.36 | 0.01 | Remainder |
| Sample No. 13 | Example | 28.5 | 7.21 | 0.83 | 0.03 | 0.24 | 0.01 | Remainder |
| Sample No. 14 | Example | 26.1 | 5.32 | 0.54 | 0.00 | 0.18 | 0.01 | Remainder |
| Sample No. 15 | Example | 27.5 | 5.84 | 0.34 | 0.02 | 0.11 | 0.01 | Remainder |
| Sample No. 16 | Example | 26.1 | 7.24 | 1.23 | 0.02 | 0.31 | 0.01 | Remainder |
| Sample No. 17 | Example | 31.9 | 6.50 | 0.71 | 0.03 | 0.46 | 0.01 | Remainder |
| Sample No. 18 | Example | 27.1 | 5.49 | 1.45 | 0.07 | 0.35 | 0.01 | Remainder |
| Sample No. 19 | Example | 26.1 | 5.11 | 0.83 | 0.04 | 0.31 | 0.02 | Remainder |
| Sample No. 20 | Example | 29.9 | 6.52 | 0.65 | 1.19 | 0.42 | 0.02 | Remainder |
| Sample No. 21 | Comparative Example | 29.1 | 5.88 | 0.71 | 0.02 | 0.01 | 0.01 | Remainder |
| Sample No. 22 | Comparative Example | 32.4 | 6.78 | 0.99 | 0.06 | 0.03 | 0.02 | Remainder |
| Sample No. 23 | Comparative Example | 33.5 | 9.27 | 0.65 | 0.13 | 0.56 | 0.01 | Remainder |
| Sample No. 24 | Comparative Example | 34.9 | 11.80 | 0.95 | 0.35 | 0.54 | 0.01 | Remainder |
| Sample No. 25 | Comparative Example | 32.2 | 6.87 | 0.78 | 0.05 | 0.03 | 0.02 | Remainder |
| Sample No. 26 | Comparative Example | 32.6 | 7.85 | 0.86 | 0.08 | 0.65 | 0.01 | Remainder |
| Sample No. 27 | Comparative Example | 29.2 | 6.11 | 0.65 | 0.04 | 0.32 | 0.02 | Remainder |
| Sample No. 28 | Comparative Example | 27.9 | 5.82 | 0.69 | 0.02 | 0.45 | 0.03 | Remainder |
| Sample No. 29 | Comparative Example | 30.1 | 6.99 | 0.61 | 0.05 | 0.39 | 0.10 | Remainder |

TABLE 2

| | | Blank material to be cut for dentistry | | | | | |
|---|---|---|---|---|---|---|---|
| | | Alloy composition | | | | | |
| | | Si/Mo | C/Si | N/Si | N/C | N impregnation method | Molding method |
| Sample No. 1 | Example | 0.115 | 0.026 | 0.167 | 6.50 | Metal nitride raw material | Powder metallurgy |
| Sample No. 2 | Example | 0.114 | 0.042 | 0.188 | 4.50 | Metal nitride raw material | Powder metallurgy |
| Sample No. 3 | Example | 0.115 | 0.036 | 0.145 | 4.00 | Metal nitride raw material | Powder metallurgy |
| Sample No. 4 | Example | 0.064 | 0.059 | 0.265 | 4.50 | Metal nitride raw material | Powder metallurgy |
| Sample No. 5 | Example | 0.109 | 0.099 | 0.324 | 3.29 | Metal nitride raw material | Powder metallurgy |
| Sample No. 6 | Example | 0.070 | 0.200 | 0.431 | 2.15 | Metal nitride raw material | Powder metallurgy |
| Sample No. 7 | Example | 0.081 | 0.368 | 0.284 | 0.77 | Metal nitride raw material | Powder metallurgy |
| Sample No. 8 | Example | 0.175 | 0.073 | 0.115 | 1.57 | Metal nitride raw material | Powder metallurgy |
| Sample No. 9 | Example | 0.162 | 0.048 | 0.145 | 3.00 | Metal nitride raw material | Powder metallurgy |
| Sample No. 10 | Example | 0.060 | 1.831 | 0.323 | 0.18 | Metal nitride raw material | Powder metallurgy |
| Sample No. 11 | Example | 0.115 | 0.064 | 0.333 | 5.20 | Metal nitride raw material | Powder metallurgy |
| Sample No. 12 | Example | 0.114 | 0.042 | 0.375 | 9.00 | Metal nitride raw material | Powder metallurgy |
| Sample No. 13 | Example | 0.115 | 0.036 | 0.289 | 8.00 | Metal nitride raw material | Powder metallurgy |
| Sample No. 14 | Example | 0.102 | 0.000 | 0.333 | — | Metal nitride raw material | Powder metallurgy |
| Sample No. 15 | Example | 0.058 | 0.059 | 0.324 | 5.50 | Metal nitride raw material | Powder metallurgy |
| Sample No. 16 | Example | 0.170 | 0.016 | 0.252 | 15.50 | Metal nitride raw material | Powder metallurgy |
| Sample No. 17 | Example | 0.109 | 0.042 | 0.648 | 15.33 | Molten metal injection | Powder metallurgy |
| Sample No. 18 | Example | 0.264 | 0.048 | 0.241 | 5.00 | Molten metal injection | Powder metallurgy |
| Sample No. 19 | Example | 0.162 | 0.048 | 0.373 | 7.75 | Molten metal injection | Powder metallurgy |
| Sample No. 20 | Example | 0.100 | 1.831 | 0.646 | 0.35 | Molten metal injection | Powder metallurgy |
| Sample No. 21 | Comparative Example | 0.121 | 0.028 | 0.014 | 0.50 | Nitrification during sintering | Powder metallurgy |
| Sample No. 22 | Comparative Example | 0.146 | 0.061 | 0.030 | 0.50 | Nitrification during sintering | Powder metallurgy |
| Sample No. 23 | Comparative Example | 0.070 | 0.200 | 0.862 | 4.31 | Nitrification during sintering | Powder metallurgy |

TABLE 2-continued

| | | Blank material to be cut for dentistry | | | | |
|---|---|---|---|---|---|---|
| | | Alloy composition | | | | |
| | | Si/Mo | C/Si | N/Si | N/C | N impregnation method | Molding method |
| Sample No. 24 | Comparative Example | 0.081 | 0.368 | 0.568 | 1.54 | Nitrification during sintering | Powder metallurgy |
| Sample No. 25 | Comparative Example | 0.114 | 0.064 | 0.038 | 0.60 | Molten metal injection | Powder metallurgy |
| Sample No. 26 | Comparative Example | 0.110 | 0.093 | 0.756 | 8.13 | Molten metal injection | Powder metallurgy |
| Sample No. 27 | Comparative Example | 0.106 | 0.062 | 0.492 | 8.00 | Molten metal injection | Casting |
| Sample No. 28 | Comparative Example | 0.119 | 0.029 | 0.652 | 22.50 | Molten metal injection | Casting |
| Sample No. 29 | Comparative Example | 0.087 | 0.082 | 0.639 | 7.80 | Molten metal injection | Casting |

In addition, in the tables, among the metal powders and the blank materials to be cut for dentistry of the Samples Nos., those corresponding to the teachings of the invention are denoted by "Example", and those that do not correspond to the invention are denoted by "Comparative Example".

2. Evaluation of Blank Material to be Cut for Dentistry 2.1 Measurement of Total Amount of Si and Content of Si Contained as Silicon Oxide For the blank material to be cut for dentistry of each of the Samples Nos., the total amount of Si and the content of Si contained as silicon oxide were measured by gravimetry and ICP atomic emission spectrometry. The measurement results are shown in Table 3.

2.2 Evaluation of Crystal Structure According to X-Ray Diffractometry

The blank material to be cut for dentistry of each of the Samples Nos. was provided for crystal structure analysis according to X-ray diffractometry. In addition, the height and the position of each peak included in the obtained X-ray diffraction pattern were collated with the database published in the ICDD card to identify the crystal structure included in the blank material. Moreover, when the height of the highest peak among the peaks caused by Co is assumed to be 1, the ratio of the height of the highest peak among the peaks caused by $Co_3Mo$ was calculated. The calculation results are shown in Table 3.

2.3. Evaluation of Pore, Dendritic Phase, and Aspect Ratio of Crystal Structure

From the blank material to be cut for dentistry of each of the Samples Nos., a test piece was machined by cutting work.

Next, the cut surface of the test piece was polished, the obtained polished surface was observed by a scanning electron microscope, and regions occupied by pores in the observation image were specified. In addition, the average diameter of the regions occupied by the pores (this is regarded as the average diameter of the pores) is measured, and the ratio of the area of the regions occupied by the pores to the entire area of the observation image (area ratio) was calculated.

In addition, by checking the ratio of a dendritic structure present in the observation image, the degree of presence of a dendritic phase was evaluated according to the following evaluation criteria.

<Evaluation Criteria of Dendritic Phase>

A: the dendritic phase is rarely present

B: a small amount of the dendritic phase is present (an area ratio of 10% or less)

C: a bit (a slightly) large amount of the dendritic phase is present (an area ratio of higher than 10% and equal to or less than 20%)

D: a very large amount of the dendritic phase is present (an area ratio of higher than 20%)

In addition, the obtained polished surface was observed by the scanning electron microscope, and the average value of the aspect ratios of the crystal structures in the observation image was calculated.

The results of the above evaluation are shown in Table 3.

2.4 Evaluation of Concentration of N

The blank material to be cut for dentistry of each of the Samples Nos. was cut along the thickness direction, and the cut surface was polished.

Next, on the polished surfaces, line analysis was performed from the surface to the inside of the blank material by the electron probe microanalyzer (EPMA). In addition, the distribution of the concentration of N in the thickness direction of the blank material was obtained.

Next, the concentration of N at a position of 0.3 mm from the surface was obtained as the concentration of N of a surface layer portion, the concentration of N at a position of 5 mm from the surface was obtained as the concentration of N of an inner layer portion, and the ratio of the concentration of N of the inner layer portion to the concentration of N of the surface layer portion was obtained. The calculation results are shown in Table 3.

2.5 Measurement of Vickers Hardness

The blank material to be cut for dentistry of each of the Samples Nos. was cut along the thickness direction, and the cut surfaces were polished.

Next, in the polished surface, the Vickers hardness thereof at a position of 0.3 mm from the surface of the blank material was measured, and this was obtained as the Vickers hardness of the surface layer portion. In addition, the Vickers hardness thereof at a position of 5 mm from the surface of the blank material was measured, and this was obtained as the Vickers hardness of the inner layer portion.

Next, the ratio of the Vickers hardness of the inner layer portion to the Vickers hardness of the surface layer portion was obtained. The calculation results are shown in Table 3.

In addition, the measurement values of the Vickers hardness of the surface layer portion are shown in Table 4.

In addition, the test load of a diamond indenter was set to 100 gf.

2.6 Evaluation of Corrosion Resistance

From the blank material to be cut for dentistry of each of the Samples Nos., a test piece was machined by cutting work.

Next, for the obtained test pieces, the amount of eluted metal ions was measured on the basis of a test method of the corrosion resistance of noble metal materials for dental metal-ceramic restorations specified in JIS T 6118 (2012).

In addition, the measurement results were evaluated on the basis of the following evaluation criteria.

<Evaluation Criteria of Corrosion Resistance>

A: corrosion resistance is very high (the amount of eluted metal ions is very small)

B: corrosion resistance is high (the amount of eluted metal ions is small)

C: corrosion resistance is low (the amount of eluted metal ions is large)

D: corrosion resistance is very low (the amount of eluted metal ions is very large)

The results of the above evaluation are shown in Table 4.

2.7 Measurement of 0.2% Proof Stress, Elongation, and Young's Modulus

From the blank material to be cut for dentistry of each of the Samples Nos., a test piece was machined by cutting work.

Next, for the obtained test pieces, the 0.2% proof stress and elongation were measured on the basis of the test method of the mechanical properties of noble metal materials for dental metal-ceramic restorations specified in JIS T 6118 (2012).

In addition, the Young's modulus was obtained on the basis of a test method of dental metallic materials specified in JIS T 6004 (2012).

The measurement results are shown in Table 4.

2.8 Measurement of Fatigue Strength

From the blank material to be cut for dentistry of the Samples Nos., a test piece was machined by cutting work.

Next, for the obtained test pieces, the fatigue strength was measured on the basis of a test method specified in JIS T 0309 (2009).

The measurement results are shown in Table 4.

2.9 Evaluation of Machinability 2.9.1 Evaluation Based on Length of Cut Waste

For the blank material to be cut for dentistry of each of the Samples Nos., machinability was evaluated as follows.

First, holes were cut from the obtained blank material by using a drilling machine. Thereafter, cut waste generated during the cutting work was recovered, and the average length thereof was measured. The average length of the cut waste being measured was evaluated according to the following evaluation criteria. In addition, in the cutting work, a drill which is made of a cemented carbide and has a diameter of 2 mm was used, and the number of revolutions was 420 revolutions per minute. In addition, a cutting oil was not used.

<Evaluation Criteria of Machinability>

A: the average length of cut waste is less than 5 mm (machinability is particularly good)

B: the average length of cut waste is equal to or greater than 5 mm and less than 10 mm (machinability is good)

C: the average length of cut waste is equal to or greater than 10 mm (machinability is slightly poor)

D: the average length of cut waste is equal to or greater than 10 mm and cut waste has a spiral shape (machinability is poor)

The results of the above evaluation are shown in Table 4.

2.9.2 Evaluation Based on Cutting Resistance

For the blank material to be cut for dentistry obtained in each of Examples and Comparative Examples, machinability was evaluated as follows.

First, the obtained blank material was fixed to the measuring unit of a three-component tool dynamometer.

Thereafter, a machining center performed the cutting work on the surface layer portion of the blank material to allow a working tool to perform scanning along the trace illustrated in FIGS. 6A and 6B. In addition, among the three-component cutting resistances measured during the cutting work, the maximum value was obtained and evaluated according to the following evaluation criteria.

<Evaluation Criteria of Cutting Resistance>

A: the cutting resistance is equal to or less than 200 N

B: the cutting resistance is higher than 200 N and is equal to or less than 250 N C: the cutting resistance is higher than 250 N and is equal to or less than 300 N D: the cutting resistance is higher than 300 N The results of the above evaluation are shown in Table 4.

The machining center performed the cutting work on the inner layer portion of the blank material to allow the working tool to perform scanning along the trace illustrated in FIGS. 6A and 6B. Among the three-component cutting resistances measured during the cutting work, the maximum value was obtained.

Next, the ratio of the cutting resistance of the inner layer portion to the cutting resistance of the surface layer portion obtained in advance was calculated. The calculation results are shown in Table 4.

2.10 Evaluation of Thermal Expansion Coefficient

From the blank material to be cut for dentistry of each of the Samples Nos., a test pieces was machined by cutting work.

Next, for the obtained test pieces, the temperature dependence of thermal expansion was obtained on the basis of a test method specified in JIS Z 2285 (2003). At this time, by repeating increasing and decreasing temperature, the stability of the temperature dependence of thermal expansion, that is, the stability of the thermal expansion coefficient was checked. In addition, the stability of the thermal expansion coefficient was evaluated according to the following evaluation criteria.

<Evaluation Criteria of Stability of Thermal Expansion Coefficient>

A: the thermal expansion coefficient is particularly stable

B: the thermal expansion coefficient is stable

C: the thermal expansion coefficient is slightly unstable

D: the thermal expansion coefficient is unstable

The results of the above evaluation are shown in Table 4.

TABLE 3

| | | Blank material to be cut for dentistry Evaluation results | | | | | | | |
|---|---|---|---|---|---|---|---|---|---|
| | | $SiO_2$/ total Si % | Ratio of height of peak in XRD — | Pore Average diameter μm | Pore Area ratio % | Inner layer portion/ surface layer portion Concentration of N % | Hardness % | Dendritic phase — | Aspect ratio — |
| Sample No. 1 | Example | 53 | 0.22 | 0.53 | 0.025 | 108 | 98 | B | 0.72 |
| Sample No. 2 | Example | 36 | 0.31 | 0.66 | 0.038 | 126 | 96 | A | 0.65 |
| Sample No. 3 | Example | 45 | 0.27 | 0.58 | 0.032 | 92 | 102 | B | 0.58 |
| Sample No. 4 | Example | 24 | 0.25 | 0.74 | 0.051 | 75 | 105 | C | 0.46 |

TABLE 3-continued

Blank material to be cut for dentistry
Evaluation results

| | | SiO$_2$/total Si % | Ratio of height of peak in XRD | Pore Average diameter μm | Pore Area ratio % | Inner layer portion/surface layer portion Concentration of N % | Inner layer portion/surface layer portion Hardness % | Dendritic phase | Aspect ratio |
|---|---|---|---|---|---|---|---|---|---|
| Sample No. 5 | Example | 49 | 0.38 | 0.35 | 0.022 | 135 | 95 | A | 0.82 |
| Sample No. 6 | Example | 32 | 0.42 | 0.89 | 0.087 | 112 | 97 | A | 0.42 |
| Sample No. 7 | Example | 28 | 0.48 | 0.97 | 0.097 | 173 | 88 | A | 0.41 |
| Sample No. 8 | Example | 66 | 0.16 | 0.45 | 0.121 | 70 | 115 | C | 0.75 |
| Sample No. 9 | Example | 77 | 0.36 | 0.43 | 0.112 | 98 | 101 | B | 0.77 |
| Sample No. 10 | Example | 55 | 0.63 | 0.75 | 0.089 | 103 | 99 | A | 0.43 |
| Sample No. 11 | Example | 53 | 0.22 | 0.53 | 0.025 | 111 | 97 | A | 0.73 |
| Sample No. 12 | Example | 36 | 0.31 | 0.66 | 0.038 | 142 | 94 | A | 0.68 |
| Sample No. 13 | Example | 45 | 0.27 | 0.58 | 0.032 | 145 | 93 | A | 0.56 |
| Sample No. 14 | Example | 24 | 0.25 | 0.74 | 0.051 | 77 | 104 | A | 0.47 |
| Sample No. 15 | Example | 18 | 0.26 | 0.76 | 0.062 | 75 | 104 | C | 0.48 |
| Sample No. 16 | Example | 84 | 0.55 | 1.05 | 0.154 | 65 | 109 | C | 0.40 |
| Sample No. 17 | Example | 49 | 0.38 | 0.35 | 0.022 | 54 | 138 | A | 0.83 |
| Sample No. 18 | Example | 66 | 0.16 | 0.45 | 0.121 | 60 | 125 | A | 0.74 |
| Sample No. 19 | Example | 77 | 0.36 | 0.43 | 0.112 | 72 | 116 | A | 0.75 |
| Sample No. 20 | Example | 55 | 0.63 | 0.75 | 0.089 | 198 | 71 | A | 0.41 |
| Sample No. 21 | Comparative Example | 19 | 0.37 | 0.75 | 0.063 | 35 | 161 | C | 0.43 |
| Sample No. 22 | Comparative Example | 6 | 0.76 | 0.25 | 0.087 | 45 | 157 | C | 0.85 |
| Sample No. 23 | Comparative Example | 17 | 0.42 | 0.89 | 0.087 | 28 | 178 | A | 0.41 |
| Sample No. 24 | Comparative Example | 15 | 0.48 | 0.97 | 0.097 | 41 | 169 | A | 0.40 |
| Sample No. 25 | Comparative Example | 25 | 0.48 | 0.25 | 0.087 | 48 | 146 | C | 0.84 |
| Sample No. 26 | Comparative Example | 28 | 0.51 | 1.05 | 0.123 | 72 | 145 | A | 0.40 |
| Sample No. 27 | Comparative Example | 93 | 0.52 | 15.2 | 1.5 | 38 | 154 | D | — |
| Sample No. 28 | Comparative Example | 1 | 0.98 | 12.5 | 1.2 | 22 | 212 | D | — |
| Sample No. 29 | Comparative Example | 2 | 1.05 | 10.3 | 1.1 | 26 | 194 | D | — |

TABLE 4

Blank material to be cut for dentistry
Evaluation results

| | | Corrosion resistance — | Vickers hardness — | 0.2% proof stress MPa | Elongation % | Young's modulus GPa | Fatigue strength MPa | Machinability Length of cut waste — | Machinability Cutting resistance of surface layer portion — | Machinability Inner layer portion/surface layer portion — | Thermal expansion coefficient — | Dental prosthesis Porcelain composition Alumina content mass % | Dental prosthesis Evaluation results Adhesion — |
|---|---|---|---|---|---|---|---|---|---|---|---|---|---|
| Sample No. 1 | Example | A | 265 | 505 | 40 | >150 | 556 | A | A | 96 | A | 15 | A |
| Sample No. 2 | Example | A | 301 | 509 | 38 | >150 | 560 | A | A | 94 | A | 15 | A |
| Sample No. 3 | Example | A | 295 | 501 | 33 | >150 | 551 | A | A | 106 | A | 15 | A |
| Sample No. 4 | Example | B | 332 | 515 | 22 | >150 | 567 | B | B | 112 | B | 15 | B |
| Sample No. 5 | Example | A | 245 | 516 | 42 | >150 | 568 | A | A | 93 | A | 15 | A |
| Sample No. 6 | Example | B | 341 | 528 | 17 | >150 | 581 | B | B | 98 | B | 15 | B |
| Sample No. 7 | Example | B | 379 | 542 | 9 | >150 | 596 | B | B | 91 | B | 15 | B |
| Sample No. 8 | Example | A | 276 | 503 | 36 | >150 | 553 | B | B | 116 | A | 15 | A |
| Sample No. 9 | Example | A | 262 | 507 | 41 | >150 | 558 | A | A | 105 | B | 15 | B |
| Sample No. 10 | Example | C | 412 | 518 | 8 | >150 | 570 | C | C | 98 | C | 15 | C |
| Sample No. 11 | Example | A | 265 | 505 | 40 | >150 | 556 | A | A | 95 | A | 15 | A |
| Sample No. 12 | Example | A | 301 | 509 | 38 | >150 | 560 | A | A | 93 | A | 15 | A |
| Sample No. 13 | Example | A | 295 | 501 | 33 | >150 | 551 | A | A | 95 | A | 15 | A |
| Sample No. 14 | Example | B | 332 | 515 | 22 | >150 | 567 | B | B | 112 | B | 15 | B |
| Sample No. 15 | Example | B | 338 | 520 | 15 | >150 | 532 | B | B | 102 | B | 15 | C |

TABLE 4-continued

Blank material to be cut for dentistry
Evaluation results

| | | Corrosion resistance — | Vickers hardness — | 0.2% proof stress MPa | Elongation % | Young's modulus GPa | Fatigue strength MPa | Machinability — Length of cut waste | Machinability — Cutting resistance of surface layer portion | Machinability — Inner layer portion/ surface layer portion | Thermal expansion coefficient — | Dental prosthesis — Porcelain composition Alumina content mass % | Dental prosthesis — Evaluation results Adhesion — |
|---|---|---|---|---|---|---|---|---|---|---|---|---|---|
| Sample No. 16 | Example | B | 432 | 556 | 7 | >150 | 514 | B | B | 105 | B | 15 | B |
| Sample No. 17 | Example | A | 308 | 516 | 32 | >150 | 568 | C | C | 145 | A | 15 | A |
| Sample No. 18 | Example | A | 289 | 503 | 36 | >150 | 553 | C | C | 136 | A | 15 | A |
| Sample No. 19 | Example | A | 296 | 507 | 41 | >150 | 558 | B | B | 128 | B | 15 | B |
| Sample No. 20 | Example | C | 456 | 518 | 8 | >150 | 570 | C | C | 65 | C | 15 | C |
| Sample No. 21 | Comparative Example | A | 546 | 415 | 7 | — | 457 | D | D | 178 | C | 15 | B |
| Sample No. 22 | Comparative Example | A | 523 | 431 | 5 | — | 474 | D | D | 168 | C | 15 | B |
| Sample No. 23 | Comparative Example | C | 534 | 335 | 3 | <150 | 369 | D | C | 197 | C | 15 | B |
| Sample No. 24 | Comparative Example | C | 524 | 342 | 3 | <150 | 376 | D | C | 184 | C | 15 | B |
| Sample No. 25 | Comparative Example | A | 503 | 445 | 9 | <150 | 490 | D | B | 132 | C | 15 | B |
| Sample No. 26 | Comparative Example | D | 546 | 398 | 3 | <150 | 438 | D | B | 131 | C | 15 | B |
| Sample No. 27 | Comparative Example | D | 565 | 326 | 4 | — | 359 | D | D | 164 | D | 15 | D |
| Sample No. 28 | Comparative Example | D | 506 | 301 | 8 | — | 331 | D | D | 225 | C | 15 | C |
| Sample No. 29 | Comparative Example | D | 495 | 297 | 12 | — | 327 | D | D | 206 | C | 15 | C |

As apparent from Tables 3 and 4, it could be seen that the blank material to be cut for dentistry corresponding to each of Examples had excellent corrosion resistance. In addition, it was recognized that the blank materials to be cut for dentistry had a desired Vickers hardness and 0.2% proof stress, elongation, and Young's modulus were relatively high.

In addition, it was recognized that the difference in the concentration of N or the difference in the hardness between the inner layer portion and the surface layer portion were relatively small.

Furthermore, due to the excellent machinability, when the blank material is provided for the cutting work, the cutting work can be smoothly performed with low cutting resistance. In addition, since variations in the cutting resistance are small, it is recognized that the blank material can be efficiently machined into a desired shape. In addition, since it is recognized that the difference in the cutting resistance between the inner layer portion and the surface layer portion is sufficiently small, from this point of view, it is recognized that the blank material to be cut for dentistry obtained in each of Embodiments can be efficiently machined into a desired shape.

In addition, it was recognized that the blank material to be cut for dentistry corresponding to each of Embodiments had contained a certain amount of silicon oxide and pores and had rarely contained the dendritic phase.

On the other hand, it was seen that the blank material to be cut for dentistry corresponding to each of Comparative Examples had low corrosion resistance, mechanical properties, and machinability.

3. Manufacturing of Dental Prosthesis

From the blank material to be cut for dentistry of each of the Samples Nos., a test piece was machined by cutting work.

Next, a paste of opaque porcelain was applied to the surface of the obtained test piece and was baked. Accordingly, test pieces of the dental prosthesis were obtained.

In addition, as the paste of opaque porcelain (an alumina content of 15 mass %), "Vintage MP" made by Shofu Inc. was used. In addition, the baking temperature was 950° C., and the temperature was maintained for 2 minutes. In addition, the baking atmosphere was a depressurized atmosphere.

4. Evaluation of Dental Prosthesis

To the test piece of the dental prosthesis obtained by fusing the opaque porcelain to the test piece machined from the blank material of each of the Samples Nos., destructive force was applied on the basis of an exfoliation and crack generation strength test of dental metal-ceramic restorations specified in JIS T 6120 (2001), and the adhesion of the porcelain layer was evaluated according to the following evaluation criteria.

<Evaluation Criteria of Exfoliation and Crack Generation Strength Test>

A: higher than 2 times of the test piece obtained from the blank material of the Sample No. 27

B: higher than 1.5 times and equal to or less than 2 times of the test piece obtained from the blank material of the Sample No. 27

C: higher than 1 time and equal to or less than 1.5 times of the test piece obtained from the blank material of the Sample No. 27

D: equal to or less than 1 time of the test piece obtained from the blank material of the Sample No. 27

The results of the above evaluation are shown in Table 4.

As apparent from Table 4, it was recognized that the dental prosthesis corresponding to each of Examples has higher adhesion of the porcelain layer compared to the dental prosthesis corresponding to each of Comparative Examples.

In addition, the dental prosthesis corresponding to each of Examples was cut, and line analysis was performed on the cross-section by the electron probe microanalyzer. As a result, it was recognized that mullite was present in a layer format the interface between the porcelain layer and the metal frame.

In addition, on the blank material corresponding to each of Examples, the HIP treatment was performed under the following conditions.

<HIP Treatment Conditions>

Heating temperature: 1100° C.
Heating time: 2 hours
Pressurization pressure: 100 MPa Next, for the blank material subjected to the HIP treatment, machinability was evaluated in the same manner as Section 2.9 described above. As a result, the machinability of the blank material subjected to the HIP treatment was slightly degraded compared to the machinability of the blank material which was not subjected to the HIP treatment. Although the detailed reasons are not clear, one of the reasons is that the hardness of the blank material was increased due to the HIP treatment.

5. Evaluation of Relationship Between Concentration of N and Hardness

First, the blank materials to be cut for dentistry of the Samples Nos. 30 to 36 having the alloy compositions shown in Table 5 were manufactured.

Next, for "2.5 Measurement of Vickers Hardness" described above, the Vickers hardness of both the surface layer portion and the inner layer portion of the blank material to be cut for dentistry of each of the Samples Nos. 30 to 36 were measured. The measurement results are shown in Table 5 and FIG. 11.

addition, as the measurement result of the concentration of N, even when the total concentration of N was changed, the concentration of N between the surface layer portion and the inner layer portion was not significantly changed.

What is claimed is:

1. A blank material to be cut for dentistry comprising:
   Co as a main component;
   Cr at a ratio equal to or higher than 26 mass % and equal to or less than 35 mass %;
   Mo at a ratio equal to or higher than 5 mass % and equal to or less than 12 mass %;
   Si at a ratio equal to or higher than 0.3 mass % and equal to or less than 2.0 mass %; and
   N at a ratio equal to or higher than 0.09 mass % and equal to or less than 0.5 mass %,
   wherein the blank material is a sintered body of a metal powder,
   the blank material includes a surface layer portion and an inner layer portion,
   the surface layer portion cross-sectionally extends through the blank material at a depth of 0.3 mm relative to an outer major surface of the blank material,
   the inner layer portion cross-sectionally extends through the blank material at a depth of 5 mm relative to the outer major surface, and
   a concentration of N at the inner layer portion is equal to or higher than 50% and equal to or less than 200% of a concentration of N at the surface layer portion.

2. The blank material to be cut for dentistry according to claim 1,
   wherein the Vickers hardness of the inner layer portion is equal to or higher than 200 and equal to or less than 480.

3. The blank material to be cut for dentistry according to claim 1,
   wherein the blank material includes a surface layer portion and an inner layer portion,
   the surface layer portion cross-sectionally extends through the blank material at a depth of 0.3 mm relative to an outer major surface of the blank material,
   the inner layer portion cross-sectionally extends through the blank material at a depth of 5 mm relative to the outer major surface, and
   a Vickers hardness at the inner layer portion is equal to or higher than 67% and equal to or less than 150% of a Vickers hardness at the surface layer portion.

TABLE 5

| | | Blank material to be cut for dentistry | | | | | | | | | |
|---|---|---|---|---|---|---|---|---|---|---|---|
| | | Alloy composition | | | | | | | Evaluation results Vickers hardness | | |
| | | Cr | Mo | Si | C | N | Ni | Co | Surface layer portion | Inner layer portion | Inner layer portion/surface layer portion |
| | | mass % | | | | | | | — | — | % |
| Sample No. 30 | Example | 29.7 | 6.84 | 0.77 | 0.02 | 0.10 | 0.01 | Remainder | 325 | 308 | 95 |
| Sample No. 31 | Example | 29.8 | 6.80 | 0.78 | 0.02 | 0.13 | 0.01 | Remainder | 315 | 302 | 96 |
| Sample No. 32 | Example | 30.2 | 6.82 | 0.79 | 0.02 | 0.15 | 0.01 | Remainder | 281 | 264 | 94 |
| Sample No. 33 | Example | 29.9 | 6.83 | 0.78 | 0.02 | 0.18 | 0.01 | Remainder | 271 | 253 | 93 |
| Sample No. 34 | Example | 30.1 | 6.85 | 0.77 | 0.02 | 0.21 | 0.01 | Remainder | 284 | 268 | 94 |
| Sample No. 35 | Example | 29.6 | 6.84 | 0.76 | 0.02 | 0.23 | 0.01 | Remainder | 380 | 355 | 93 |
| Sample No. 36 | Example | 29.7 | 6.81 | 0.78 | 0.02 | 0.27 | 0.01 | Remainder | 394 | 368 | 93 |

Figure 11:
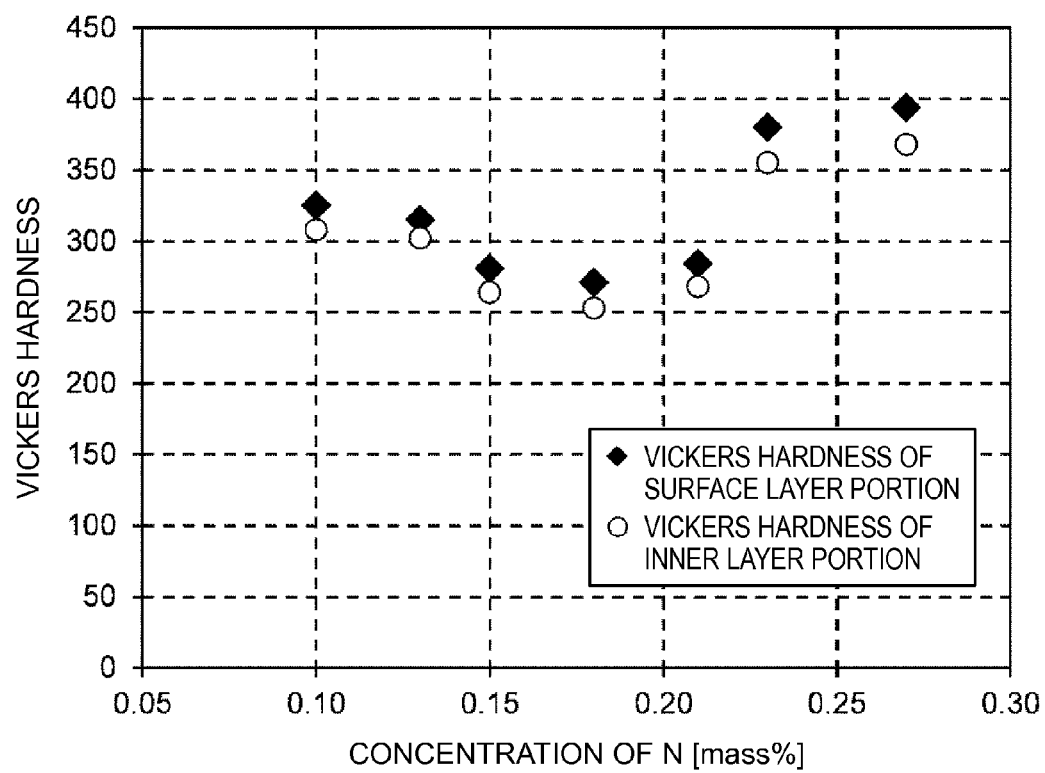
FIG. 11 is a graph showing the relationship between the concentration of N in the blank material to be cut for dentistry of each of Samples Nos. 30 to 36 and the Vickers hardness of both a surface layer portion and an inner layer portion.

As apparent from Table 5 and FIG. 11, the relationship between the concentration of N in the blank material and the Vickers hardness thereof in which hardness was extremely low at a specific concentration of N was recognized. As described above, as the hardness decreases, the toughness of the blank material was increased and thus the enhancement in the tensile strength and the proof stress was achieved. In 4. The blank material to be cut for dentistry according to claim 1,
wherein a ratio of an N content to a Si content is equal to or higher than 0.1 and equal to or less than 0.8.

5. The blank material to be cut for dentistry according to claim 1,
wherein a portion of the Si is contained as a silicon oxide, and
a ratio of Si contained as the silicon oxide to the Si is equal to or higher than 10 mass % and equal to or less than 90 mass %.

6. The blank material to be cut for dentistry according to claim 5,
wherein the silicon oxide segregates to a grain boundary of the sintered body.

7. The blank material to be cut for dentistry according to claim 1,
wherein, in an X-ray diffraction pattern obtained by X-ray diffractometry using CuKα radiation, when a height of a highest peak among peaks caused by Co identified based on an ICDD card is 1, a ratio of a height of a highest peak among peaks caused by $Co_3Mo$ identified based on the ICDD card is equal to or higher than 0.01 and equal to or less than 0.5.

8. The blank material to be cut for dentistry according to claim 1,
wherein the blank material to be cut for dentistry has a 0.2% proof stress equal to or higher than 450 MPa, an elongation equal to or higher than 2%, and a Young's modulus equal to or higher than 150 GPa.

9. The blank material to be cut for dentistry according to claim 1,
wherein the Cr content is equal to or higher than 28 mass % and equal to or less than 33 mass %.

10. The blank material to be cut for dentistry according to claim 1,
wherein the Mo content equal to or higher than 6 mass % and equal to or less than 9 mass %.

11. The blank material to be cut for dentistry according to claim 1,
wherein a mass ratio of the Si to the Mo is equal to or higher than 0.05 and equal to or less than 0.2.

12. The blank material to be cut for dentistry according to claim 1,
wherein a mass ratio of the N to the Si is equal to or higher than 0.1 and equal to or less than 0.8.

13. A metal powder for powder metallurgy comprising:
Co as a main component;
Cr at a ratio equal to or higher than 26 mass % and equal to or less than 35 mass %;
Mo at a ratio equal to or higher than 5 mass % and equal to or less than 12 mass %;
Si at a ratio equal to or higher than 0.3 mass % and equal to or less than 2.0 mass %; and
N at a ratio equal to or higher than 0.09 mass % and equal to or less than 0.5 mass %,
wherein the metal powder is used to manufacture a blank material to be cut for dentistry,
the blank material includes a surface layer portion and an inner layer portion,
the surface layer portion cross-sectionally extends through the blank material at a depth of 0.3 mm relative to an outer major surface of the blank material,
the inner layer portion cross-sectionally extends through the blank material at a depth of 5 mm relative to the outer major surface, and
a concentration of N at the inner layer portion is equal to or higher than 50% and equal to or less than 200% of a concentration of N at the surface layer portion.

14. A metal frame for porcelain fusing for dentistry comprising:
Co as a main component;
Cr at a ratio equal to or higher than 26 mass % and equal to or less than 35 mass %;
Mo at a ratio equal to or higher than 5 mass % and equal to or less than 12 mass %;
Si at a ratio equal to or higher than 0.3 mass % and equal to or less than 2.0 mass %; and
N at a ratio equal to or higher than 0.09 mass % and equal to or less than 0.5 mass %,
wherein the metal frame is machined from a cut blank material which is a sintered body of a metal powder,
the blank material includes a surface layer portion and an inner layer portion,
the surface layer portion cross-sectionally extends through the blank material at a depth of 0.3 mm relative to an outer major surface of the blank material,
the inner layer portion cross-sectionally extends through the blank material at a depth of 5 mm relative to the outer major surface, and
a concentration of N at the inner layer portion is equal to or higher than 50% and equal to or less than 200% of a concentration of N at the surface layer portion.

15. A dental prosthesis comprising:
the metal frame for porcelain fusing for dentistry according to claim 14; and
a porcelain layer provided on a surface of the metal frame.

16. The dental prosthesis according to claim 15,
wherein the porcelain layer contains alumina, and
a mullite phase is between the metal frame and the porcelain layer.

* * * * *